(12) United States Patent
Gunji

(10) Patent No.: US 11,774,462 B2
(45) Date of Patent: Oct. 3, 2023

(54) PRE-PROCESSING SYSTEM

(71) Applicant: SHIMADZU CORPORATION, Kyoto (JP)

(72) Inventor: Masahide Gunji, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 912 days.

(21) Appl. No.: 16/479,700

(22) PCT Filed: Jan. 30, 2018

(86) PCT No.: PCT/JP2018/002999
§ 371 (c)(1),
(2) Date: Jul. 22, 2019

(87) PCT Pub. No.: WO2018/143208
PCT Pub. Date: Aug. 9, 2018

(65) Prior Publication Data
US 2021/0333300 A1     Oct. 28, 2021

(30) Foreign Application Priority Data
Feb. 3, 2017    (JP) ................................ 2017-019063

(51) Int. Cl.
    *G01N 35/10*      (2006.01)
    *C12M 1/00*       (2006.01)
               (Continued)

(52) U.S. Cl.
CPC ............. *G01N 35/10* (2013.01); *C12M 47/00* (2013.01); *G01N 35/1004* (2013.01); *G01N 1/00* (2013.01);
(Continued)

(58) Field of Classification Search
CPC ...... G01N 35/10; G01N 35/1004; G01N 1/00; G01N 30/20; G01N 30/24; G01N 35/08;
(Continued)

(56) References Cited

U.S. PATENT DOCUMENTS

| | | | | |
|---|---|---|---|---|
| 6,149,818 A | * | 11/2000 | Nakamura | ............. G01N 30/40 210/656 |
| 2005/0158215 A1 | * | 7/2005 | Iwata | .................... B01L 3/0241 210/198.2 |

(Continued)

FOREIGN PATENT DOCUMENTS

| CN | 204807564 U | 11/2015 |
|---|---|---|
| JP | 2000-121650 A | 4/2000 |

(Continued)

OTHER PUBLICATIONS

International Search Report of PCT/JP2018/002999 dated Apr. 24, 2018 [PCT/ISA/210].

(Continued)

*Primary Examiner* — Jill A Warden
*Assistant Examiner* — Curtis A Thompson
(74) *Attorney, Agent, or Firm* — Sughrue Mion, PLLC

(57) ABSTRACT

In a pre-processing system, a state in which a sample dispensing probe 20a and a syringe pump 81 communicate with each other through a channel 91 and a state in which the sample dispensing probe 20a and a culture tank 301 communicate with each other through the channels 91, 93, and 94 can be switched by operation of the three-way valves 82 and 83. For this reason, the liquid sample in the culture tank 301 can be automatically discharged from the sample dispensing probe 20a without requiring the user to directly sample the liquid sample. As a result, in the pre-processing system, the user's manual sampling work can be omitted, and the user's work can be simplified.

3 Claims, 22 Drawing Sheets

(51) Int. Cl.
- *G01N 35/00* (2006.01)
- *G01N 35/08* (2006.01)
- *G01N 1/00* (2006.01)
- *G01N 30/20* (2006.01)
- *G01N 30/24* (2006.01)

(52) U.S. Cl.
CPC ............. *G01N 30/20* (2013.01); *G01N 30/24* (2013.01); *G01N 35/08* (2013.01); *G01N 2035/00475* (2013.01)

(58) Field of Classification Search
CPC ......... G01N 2035/00475; G01N 35/00; G01N 35/1009; C12M 47/00; C12M 33/00
See application file for complete search history.

(56) References Cited

U.S. PATENT DOCUMENTS

| | | | | |
|---|---|---|---|---|
| 2008/0134804 A1* | 6/2008 | Maeda | ............... | G01N 35/1097 73/863.01 |
| 2008/0229809 A1* | 9/2008 | Hirayama | ............... | G01N 30/24 73/61.55 |
| 2011/0198272 A1* | 8/2011 | Yamazaki | ............... | G01N 30/82 210/138 |
| 2014/0030168 A1* | 1/2014 | Tokumaru | ............... | B01L 3/021 422/509 |
| 2017/0160273 A1* | 6/2017 | Nogami | ................. | G01N 15/12 |

FOREIGN PATENT DOCUMENTS

| | | |
|---|---|---|
| JP | 2001-242181 A | 9/2001 |
| JP | 2016-205996 A | 12/2016 |

OTHER PUBLICATIONS

Written Opinion of PCT/JP2018/002999 dated Apr. 24, 2018 [PCT/ISA/237].

Communication dated Nov. 15, 2021, issued by the State Intellectual Property Office of the P.R.C. in application No. 201880006497.4.

Communication dated May 31, 2021 from the China National Intellectual Property Administration in CN Application No. 201880006497.4.

* cited by examiner

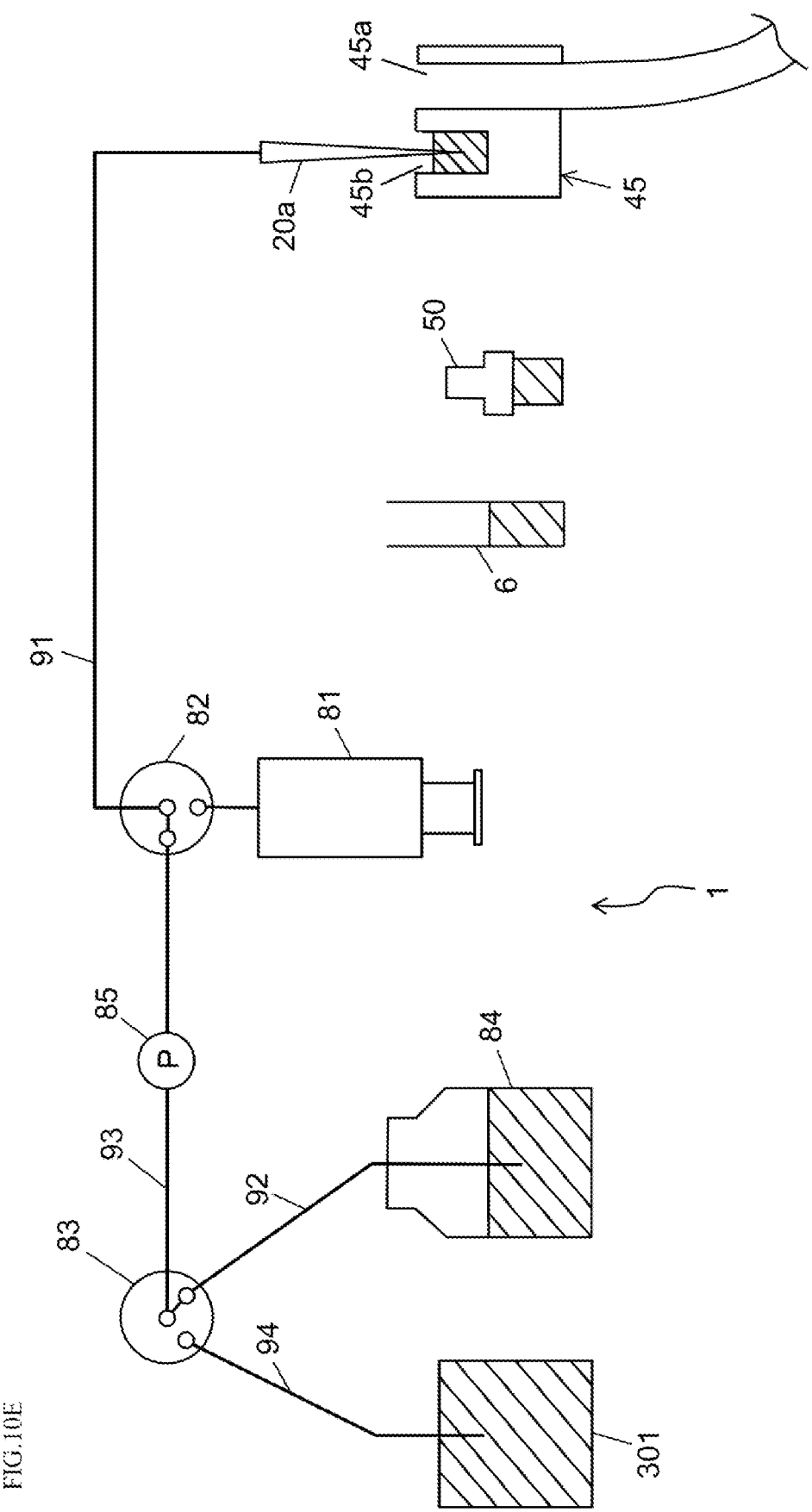

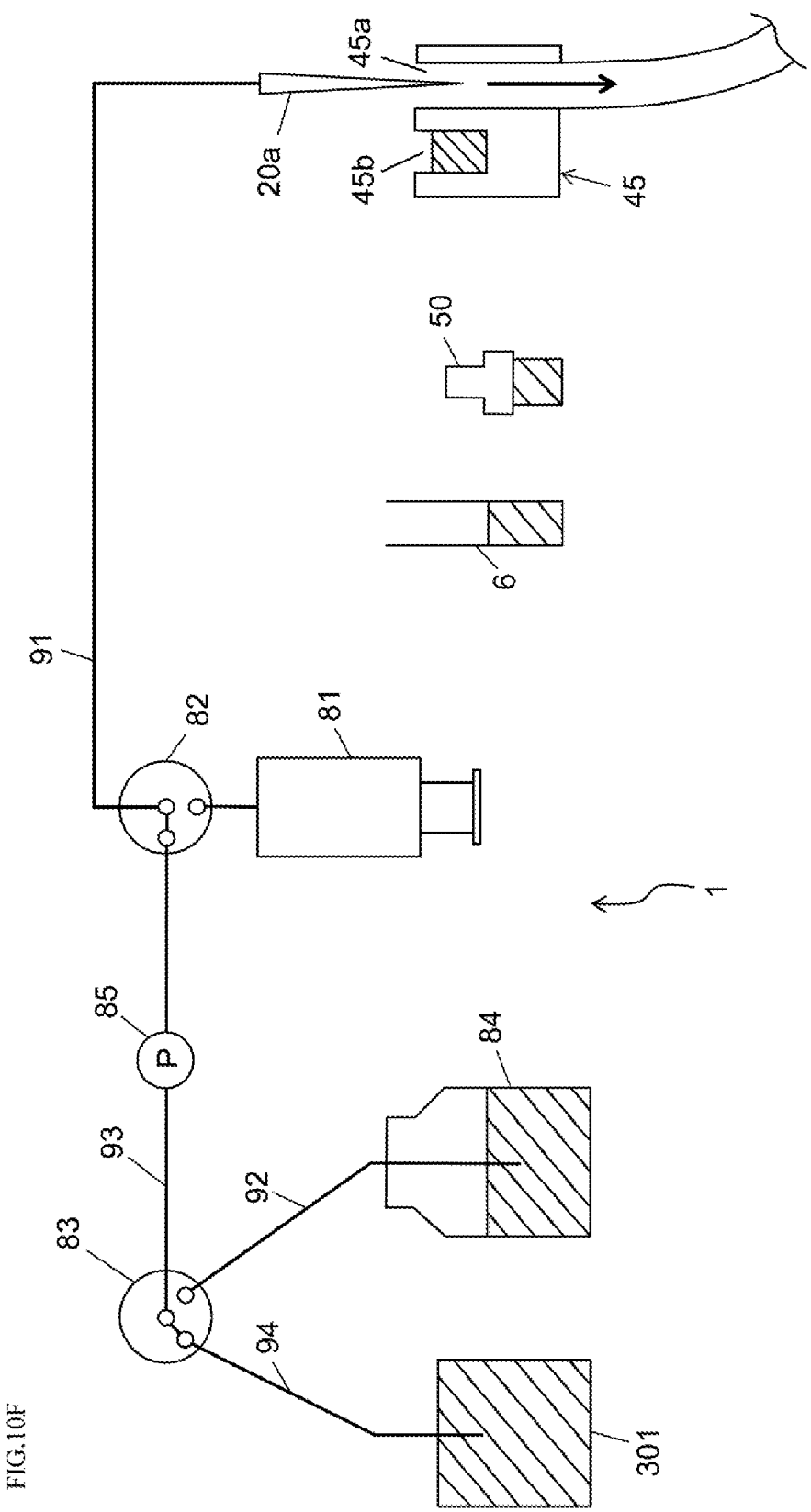

PRE-PROCESSING SYSTEM

CROSS REFERENCE TO RELATED APPLICATIONS

This application is a National Stage of International Application No. PCT/JP2018/002999, filed Jan. 30, 2018, claiming priority to Japanese Patent Application No. 2017-019063, filed Feb. 3, 2017.

TECHNICAL FIELD

The present invention relates to a pre-processing system for performing pre-processing of a liquid sample.

BACKGROUND ART

Conventionally, to make analysis on components contained in a sample, a pre-processing system that performs pre-processing of the sample has been used. For example, pre-processing, such as deproteinization, is performed for a liquid sample (medium sample) introduced from a cell culture apparatus. In such a pre-processing system, a liquid sample is dispensed from a sample container, and pre-processing is performed on the dispensed liquid sample.

When the liquid sample is dispensed, a suction operation and a discharge operation using a probe are performed. Specifically, a tip of the probe is inserted into the sample container so as to be immersed in the liquid sample. By driving a pump in this state, the liquid sample is sucked into the probe. After that, the probe is moved to a dispensing position, and the pump is driven again. In this manner, the liquid sample is discharged from the tip of the probe to the dispensing position (for example, see Patent Document 1 below).

PRIOR ART DOCUMENT

Patent Document

Patent Document 1: JP 2000-121650 A

SUMMARY OF THE INVENTION

Problems to be Solved by the Invention

In the conventional pre-processing system as described above, there has been possibility that work of the user is complicated. Specifically, in a case of using a conventional pre-processing system in order to perform pre-processing on a liquid sample, the user needs to manually inject the liquid sample into a sample container, and set the sample container to the pre-processing system. For example, in a case of performing analysis by sampling a liquid sample in a certain cycle, the user needs to sample the liquid sample in a sample container and set the sample container in the pre-processing system every cycle, which complicates the work.

The present invention has been made in view of the above-mentioned circumstances, and it is an object of the present invention to provide a pre-processing system capable of simplifying work of the user in pre-processing of a liquid sample.

Means for Solving the Problems (1) A pre-processing system according to the present invention is a pre-processing system for performing pre-processing for a liquid sample from a liquid sample storage unit. The pre-processing system includes a sample setting unit, a probe, a pump, and a switching unit. A sample container is installed in the sample setting unit. The probe sucks a liquid sample from the inside of a sample container installed in the sample setting unit and discharges the liquid sample to a dispensing position. The pump is driven when a liquid sample is sucked to and discharged from the probe. The switching unit switches to a state in which the probe communicates with the pump, or a state in which the probe communicates with the liquid sample storage unit.

According to such a configuration, it is possible to switch between the state in which the probe communicates with the pump and the state in which the probe communicates with the liquid sample storage unit by operation of the switching unit. That is, by the operation of the switching unit, it is possible to switch to a state in which a liquid sample is introduced from the liquid sample storage unit to the probe.

In the pre-processing system, if a state in which a liquid sample is introduced from the liquid sample storage unit to the probe is set by operation of the switching unit, the liquid sample in the liquid sample storage unit can be discharged automatically from the probe without direct sampling performed by the user.

Therefore, in the pre-processing for a liquid sample, the user's manual sampling work can be omitted, and the user's work can be simplified.

(2) Further, the pre-processing system may further include a dispensing control unit. The dispensing control unit causes the probe to be in a state of communicating with the pump by switching the switching unit after a liquid sample is introduced to a sample container installed in the sample setting unit via the probe in a state where the probe communicates with the liquid sample storage unit, and, in this state, drives the pump so that a liquid sample is sucked from the inside of the sample container to the probe.

According to such a configuration, operation of introducing a liquid sample from the liquid sample storage unit to the sample container via the probe, and operation of causing the liquid sample to be sucked from the inside of the sample container to the probe can be switched automatically and implemented under the control of the dispensing control unit.

For this reason, a series of operations in the pre-processing system can be automated, and the work of the user can be further simplified.

(3) Further, at the dispensing position, a separation container that separates a specific component in a liquid sample by filtering the liquid sample may be installed. The dispensing control unit may move the probe, which has sucked a liquid sample, to the dispensing position, and drive the pump to discharge the liquid sample from the probe to the separation container.

According to such a configuration, the dispensing control unit causes a liquid sample to be discharged from the probe to the separation container, so that a specific component in the liquid sample can be separated in the separation container.

Therefore, in the pre-processing system, the operations from introducing a liquid sample into the probe to separating a specific component in the liquid sample can be automated.

(4) Further, the pre-processing system may further include a cleaning solution storage unit. The cleaning solution storage unit stores a cleaning solution. The switching unit may switch to a state in which the probe communicates with the pump, a state in which the probe communicates with the liquid sample storage unit, or a state in which the probe communicates with the cleaning solution storage unit.

According to such a configuration, in the pre-processing system, it is possible to switch from the state in which the probe communicates with the pump or the state in which the probe communicates with the liquid sample storage unit, to the state in which the probe communicates with the cleaning solution storage unit by operation of the switching unit.

Therefore, a cleaning solution in the cleaning solution storage unit can be automatically introduced into the probe.

(5) Further, the pre-processing system may further include a cleaning control unit. The cleaning control unit cleans a channel from the cleaning solution storage unit to the probe by introducing a cleaning solution into the probe in a state in which the probe communicates with the cleaning solution storage unit.

According to such a configuration, in the pre-processing system, the operation of introducing a cleaning solution into the probe and cleaning a channel from the cleaning solution storage unit to the probe can be automated.

(6) In addition, the liquid sample storage unit may be a culture medium storage unit provided in a cell culture apparatus.

According to such a configuration, in the pre-processing for a culture medium (liquid sample) in the cell culture apparatus, the user's manual sampling work can be omitted, and the user's work can be simplified.

Effects of the Invention

According to the present invention, it is possible to switch from the state in which the probe communicates with the pump to the state in which the probe communicates with the liquid sample storage unit by operation of the switching unit. For this reason, a liquid sample in the liquid sample storage unit can be automatically discharged from the probe without requiring the user to directly sample the liquid sample. As a result, the user's work can be simplified in the pre-processing for a liquid sample.

BRIEF DESCRIPTION OF THE DRAWINGS

FIG. 10E is a diagram schematically showing a configuration example of the pre-processing system, showing a state in which an outer surface of the sample dispensing probe is cleaned.

FIG. 10F is a diagram schematically showing a configuration example of the pre-processing system, showing a state in which sections from a culture tank to the sample dispensing probe are filled with a liquid sample.

MODE FOR CARRYING OUT THE INVENTION

1. Overall Configuration of Analysis System

Figure 1:
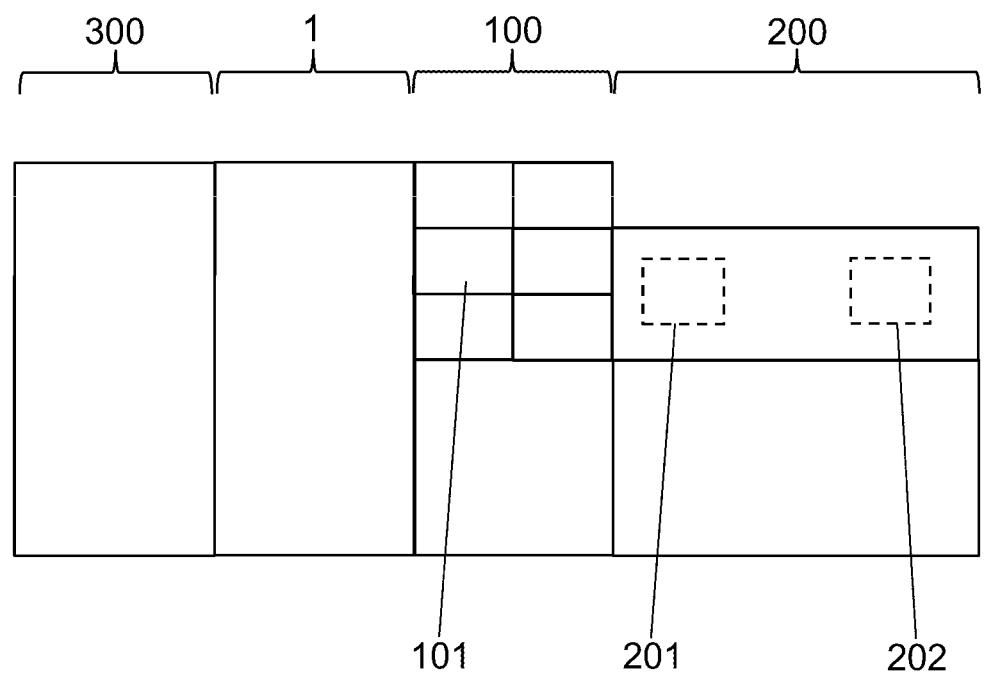
FIG. 1 is a schematic front view showing a configuration example of an analysis system including a pre-processing system according to an embodiment of the present invention.

FIG. 1 is a schematic front view showing a configuration example of an analysis system including a pre-processing system according to an embodiment of the present invention. The analysis system includes a pre-processing apparatus 1, a liquid chromatograph (LC) 100, a mass spectrometer (MS) 200, and a cell culture apparatus 300. In this analysis system, a liquid sample in the cell culture apparatus 300 is introduced into the pre-processing apparatus 1, and the pre-processing apparatus 1 executes pre-processing on the liquid sample. Then, the liquid sample subjected to the pre-processing is sequentially introduced to the LC 100 and the MS 200 to perform analysis. In this analysis system, a pre-processing system is configured with the pre-processing apparatus 1 and the cell culture apparatus 300.

The cell culture apparatus 300 is an apparatus for culturing cells in a culture medium, and the culture medium in which the cells are cultured is introduced into the pre-processing apparatus 1 as a liquid sample, and the pre-processing is performed in the pre-processing apparatus 1.

In the analysis system, the pre-processing apparatus 1 is connected to a liquid chromatograph mass spectrometer (LC/MS). However, the present invention is not limited to such a configuration, and may have a configuration in which a liquid sample for which the pre-processing is executed by the pre-processing apparatus 1 is introduced into only one of the LC 100 and the MS 200 by omitting one of the LC 100 and the MS 200.

The pre-processing apparatus 1 functions as a dispensing apparatus that dispenses a liquid sample and a reagent to be mixed with the liquid sample at a dispensing position, and performs a variety of types of pre-processing, such as filtration, stirring, and temperature control to the liquid sample and the reagent dispensed at the dispensing position. The liquid sample after the above pre-processing is performed is introduced into the LC 100 via an autosampler 101 provided in the LC 100.

The LC 100 is equipped with a column (not shown), and sample components separated in a process in which the liquid sample passing through the column are sequentially introduced into the MS 200. The MS 200 includes an ionization unit 201 that ionizes a liquid sample introduced from the LC 100, and a mass spectrometry unit 202 that analyzes an ionized liquid sample.

2. Configuration of Pre-Processing Apparatus

Figure 2:
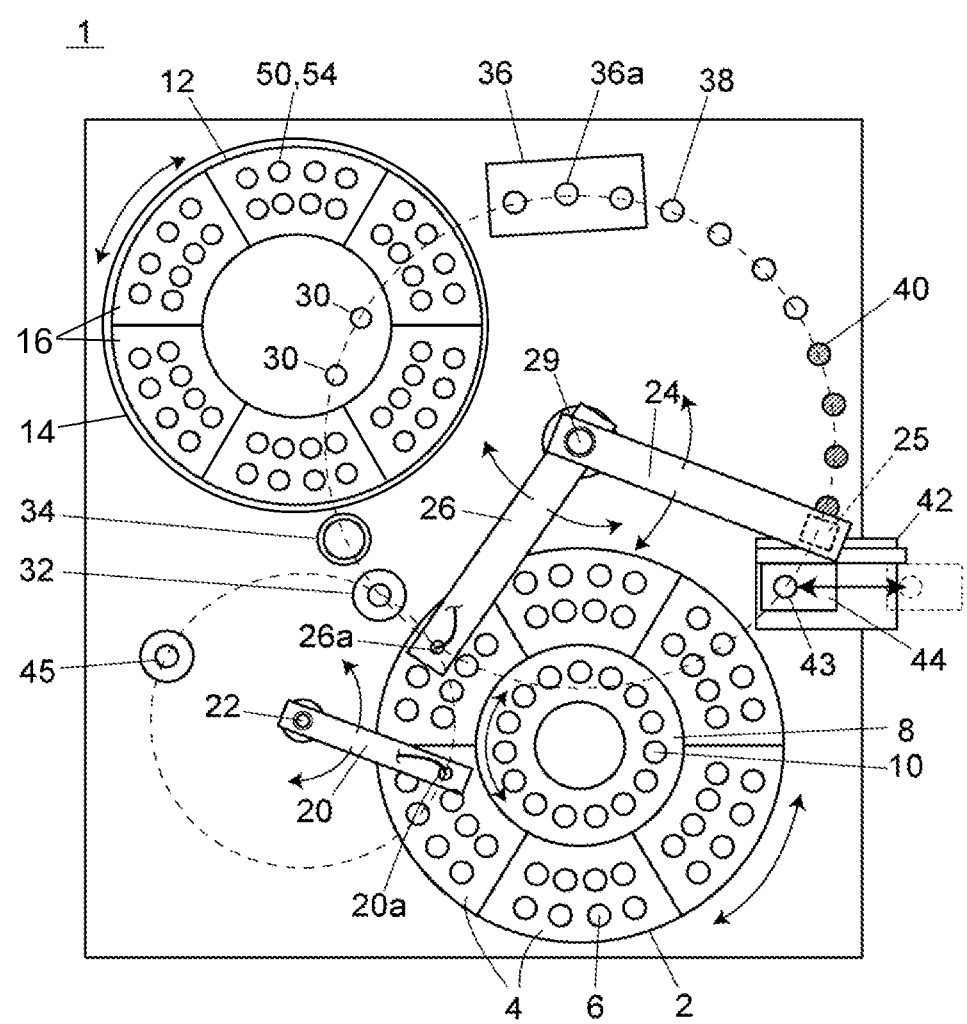
FIG. 2 is a plan view showing a configuration example of a pre-processing apparatus.

FIG. 2 is a plan view showing a configuration example of the pre-processing apparatus 1. The pre-processing apparatus 1 uses one set of a pre-processing kit consisting of a combination of a separation container 50 and a recovery container 54 for each sample, and executes pre-processing (filtering, stirring, temperature control, and the like) set for each pre-processing kit.

The pre-processing apparatus 1 is provided with a dispensing port 32 as a dispensing position as well as a plurality of processing ports for executing pre-processing on a liquid sample dispensed to the dispensing port 32. In this manner, by installing the pre-processing kit containing a liquid sample in any of the processing ports, pre-processing corresponding to each processing port is executed on the liquid sample contained in the pre-processing kit.

As the processing ports, a filtration port 30, a discard port 34, a stirring port 36*a*, a temperature control ports 38 and 40, a transfer port 43, a cleaning port 45, and the like are provided in association with each pre-processing. The processing ports each constitute a plurality of pre-processing units that each execute a plurality of types of pre-processing.

The separation container 50 and the recovery container 54 constituting the pre-processing kit are carried between the processing ports by a carrying arm 24 as a carrying unit. A holding portion 25 for holding the separation container 50 and the recovery container 54 is formed on a tip end side of the carrying arm 24. A proximal end side of the carrying arm 24 is rotatably held around a vertical shaft 29. The carrying arm 24 extends in a horizontal direction, and rotates around the vertical shaft 29, so that the holding portion 25 moves so as to draw an arc-like path in a horizontal plane. The processing ports to which the separation container 50 and the recovery container 54 are carried, and the other ports are all provided on the arc-shaped path drawn by the holding portion 25.

A liquid sample is dispensed from a sample container 6 into the pre-processing kit. A plurality of the sample containers 6 in which the liquid sample is contained can be installed in a sample setting unit 2, and samples are sequentially taken from the sample containers 6 using a sample dispensing arm 20. A plurality of sample racks 4 holding a plurality of the sample containers 6 are arranged in an annular shape in the sample setting unit 2. The sample setting unit 2 moves the sample racks 4 in a circumferential direction by rotating in a horizontal plane. In this manner, sample containers 6 can be sequentially moved to a predetermined sampling position.

Here, the sampling position is located in a path of a sample dispensing probe 20*a* as an example of the probe provided at the tip of the sample dispensing arm 20, and the sample dispensing probe 20*a* sucks a liquid sample from the sample container 6 at the sampling position. The liquid sample in the sample container 6 is sucked by the sample dispensing probe 20*a* and then discharged to the separation container 50 installed in the dispensing port 32. A discharge amount of the liquid sample to the separation container 50 is, for example, about 10 to 100 µL, and preferably about 50 µL.

The sample dispensing arm 20 is rotatable in a horizontal plane centering on a vertical shaft 22 provided on a proximal end side, and is vertically movable along the vertical shaft 22. The sample dispensing probe 20*a* is held so as to extend vertically downward at the tip of the sample dispensing arm 20, and performs movement in an arc-like path in a horizontal plane or upward and downward movement in the vertical direction according to operation of the sample dispensing arm 20.

The dispensing port 32 is provided at a position on the path of the sample dispensing probe 20*a* and on the path of the holding portion 25 of the carrying arm 24. The dispensing port 32 is a port for dispensing a sample from the sample dispensing probe 20*a* to the separation container 50 that is unused. The unused separation container 50 is carried by the carrying arm 24 to the dispensing port 32.

A reagent setting unit 8 for setting a reagent container 10 is provided at a central portion of the sample setting unit 2 in which the sample rack 4 is arranged in an annular shape. A reagent in the reagent container 10 set in the reagent setting unit 8 is collected using a reagent dispensing arm 26. The reagent dispensing arm 26 has its proximal end supported by the vertical shaft 29 shared with the carrying arm 24, is rotatable in a horizontal plane about the vertical shaft 29, and is vertically movable along the vertical shaft 29 in the vertical direction.

A reagent dispensing probe 26*a* is held at a tip of the reagent dispensing arm 26 so as to extend vertically downward. The reagent dispensing probe 26*a* performs movement in the same arc-like path as that of the holding portion 25 of the carrying arm 24 in a horizontal plane or upward and downward movement in the vertical direction according to operation of the reagent dispensing arm 26.

The reagent setting unit 8 is rotatable in the horizontal plane independently of the sample setting unit 2. A plurality of the reagent containers 10 are arranged in an annular shape in the reagent setting unit 8, and the reagent containers 10 move in the circumferential direction as the reagent setting unit 8 rotates. In this manner, the desired reagent container 10 can be moved to a predetermined reagent collecting position.

Here, the reagent collecting position is located in a path of the reagent dispensing probe 26*a* provided at the tip of the reagent dispensing arm 26, and the reagent dispensing probe 26*a* sucks a reagent from the reagent container 10 at the reagent collecting position. The reagent in the reagent container 10 is sucked by the reagent dispensing probe 26*a* and then discharged to the separation container 50 installed in the dispensing port 32 so as to be added to a sample in the separation container 50.

The separation container 50 and the recovery container 54 are held by a container holding unit 12 provided at a position different from the sample setting unit 2 and the reagent setting unit 8. In the container holding unit 12, a plurality of sets of the pre-processing kits in a state, in which the separation container 50 and that recovery container 54 that are unused are stacked, are arranged in an annular shape. The container holding unit 12 includes a rotation unit 14 that rotates in a horizontal plane, and a plurality of container racks 16 that can be attached to and detached from the rotation unit 14.

Each of the container racks 16 can hold a plurality of the pre-processing kits. A plurality of the container racks 16 are arranged in an annular shape on the rotation unit 14. A plurality of the container racks 16 arranged in an annular shape form an annular holding area for holding a plurality of the pre-processing kits. The rotation unit 14 displaces container racks 16 in the circumferential direction of the holding area by rotating in the horizontal plane. In this manner, a plurality of the pre-processing kits can be sequentially moved to a predetermined carrier position. Here, the carrier position is located on the path of the holding portion 25 provided at the tip of the carrying arm 24. The holding portion 25 holds the separation container 50 or the recovery container 54 at the carrier position, and carries them to a port as a carrier destination.

As described above, the pre-processing kit is dividedly held in a plurality of the container racks 16. In this manner, each of the container racks 16 can be individually attached to and detached from the rotation unit 14. In this manner, even in a case where the separation container 50 or the recovery container 54 held in any of the container racks 16 is being processed, the other container racks 16 can be attached or detached to perform another operation. Therefore, the pre-processing efficiency can be improved.

However, the configuration of the separation container 50 and the recovery container 54 is not limited to one in which they are held by the container holding unit 12 with the container rack 16 interposed between them, and may be one in which, for example, they are directly held by the container holding unit 12. Further, the configuration of the separation container 50 and the recovery container 54 is not limited to one in which they are held by the container holding unit 12 in a state of being placed on top of each other, and may be one in which the separation container 50 and the recovery container 54 are held individually. Furthermore, the configuration of a plurality of the container racks 16 is not limited to one in which they are arranged in an annular shape, and may be one in which, for example, they are arranged in an arc. In this case, a plurality of the separation containers 50 and the recovery containers 54 are held in an arc-like holding area, which is not annular.

In the container holding unit 12, an analyst can set a plurality of types (for example, two types) of the separation containers 50 provided with separation layers having different separation performances. These separation containers 50 are used properly according to analysis items of a sample, and the separation container 50 corresponding to an analysis item designated by an analyst is selected and carried from the container holding unit 12. Here, the analysis item is a type of analysis that is continuously performed using a sample subjected to pre-processing in the pre-processing apparatus 1, and is, for example, a type of analysis that is performed by the LC 100 or the MS 200.

Figure 3A:
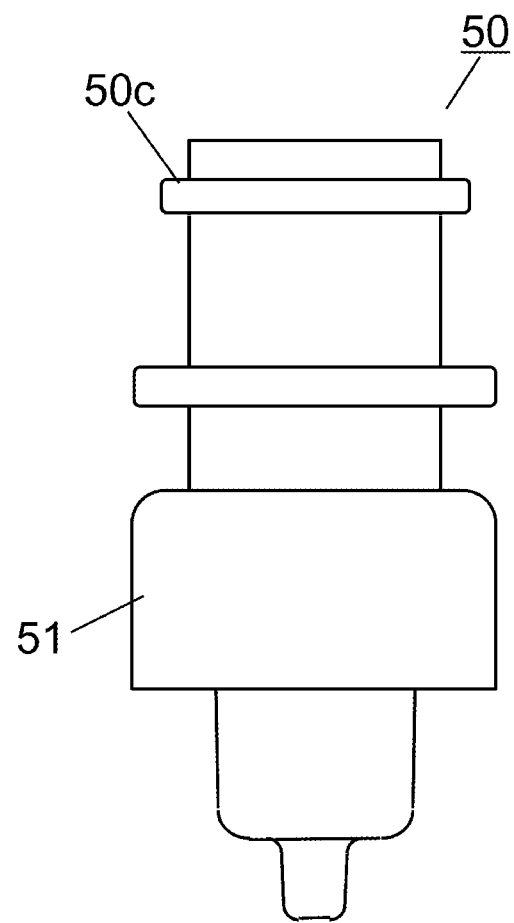
FIG. 3A is a side view showing a configuration example of a separation container.
Figure 3B:
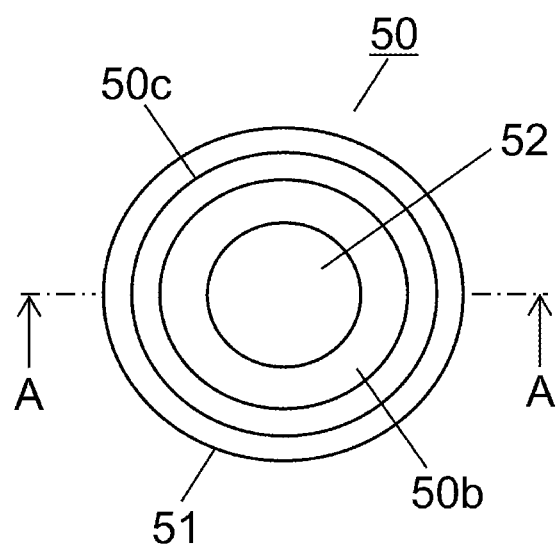
FIG. 3B is a plan view of the separation container of FIG. 3A.
Figure 3C:
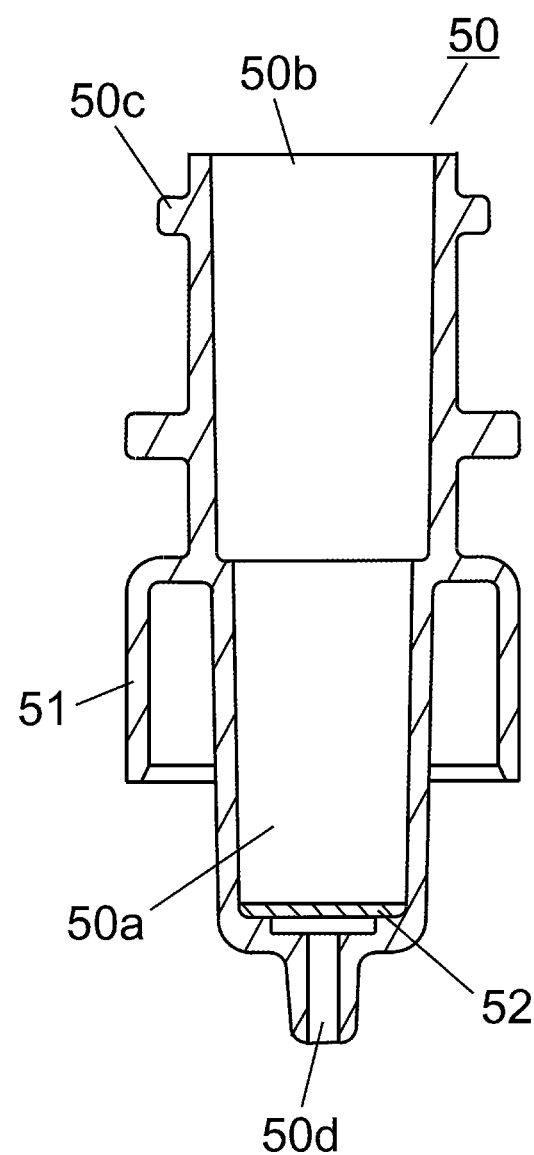
FIG. 3C is a cross-sectional view showing a cross section taken along line A-A of FIG. 3B.
Figure 4A:
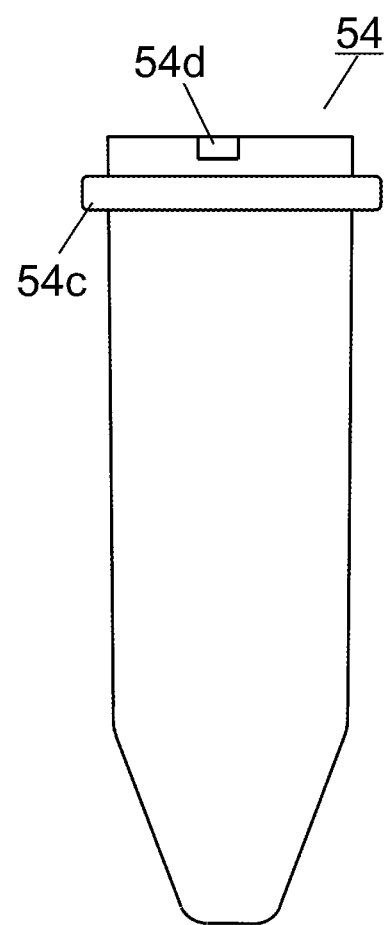
FIG. 4A is a side view showing a configuration example of a recovery container.
Figure 4B:
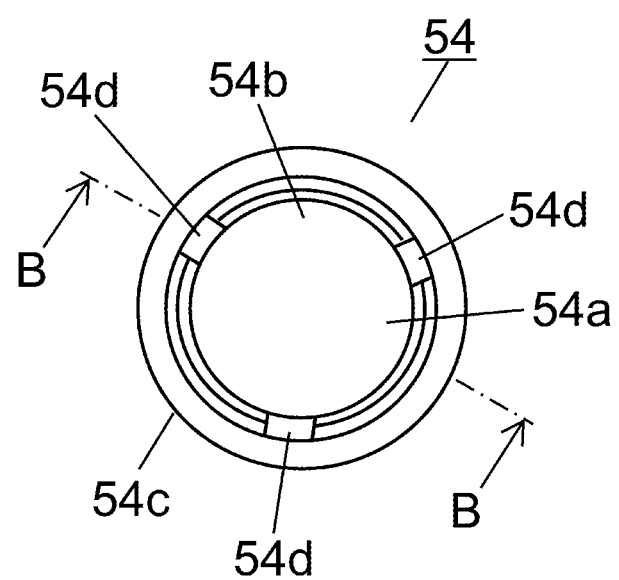
FIG. 4B is a plan view of the recovery container of FIG. 4A.
Figure 4C:
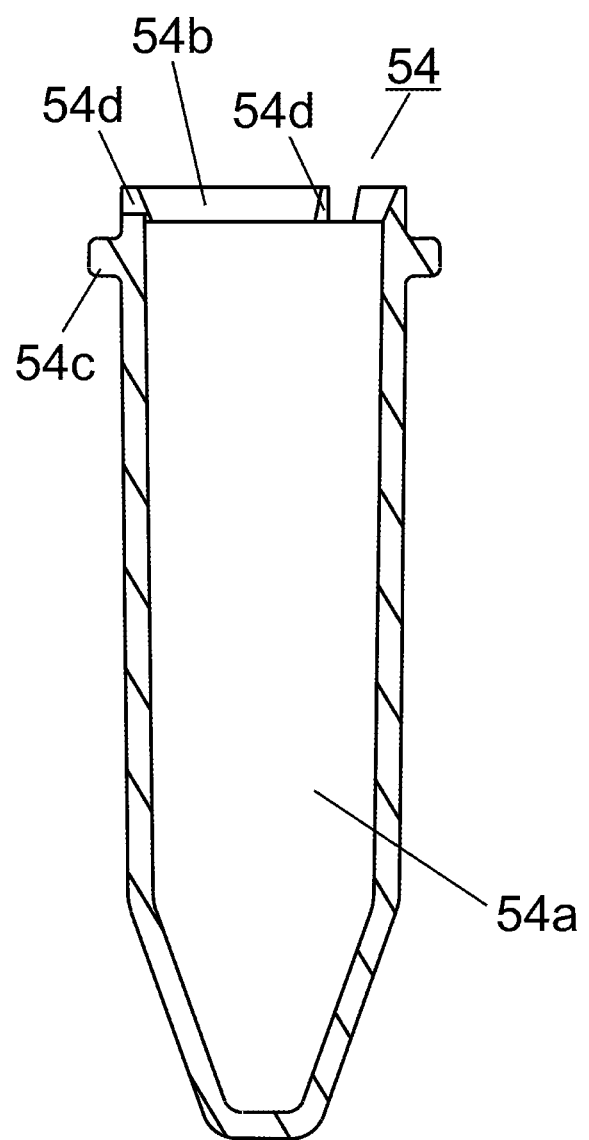
FIG. 4C is a cross-sectional view showing a cross section taken along line B-B of FIG. 4B.
Figure 5:
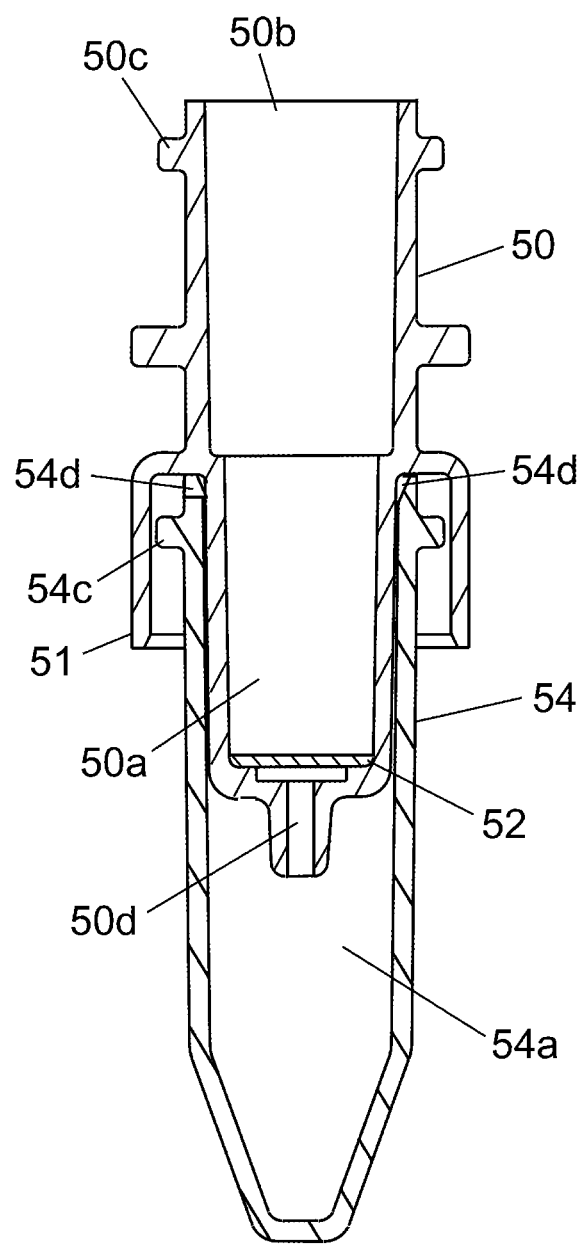
FIG. 5 is a cross-sectional view showing a pre-processing kit in a state in which the separation container and the recovery container are placed on top of each other.

FIG. 3A is a side view showing a configuration example of the separation container 50. FIG. 3B is a plan view of the separation container 50 of FIG. 3A. FIG. 3C is a cross-sectional view showing a cross section taken along line A-A of FIG. 3B. FIG. 4A is a side view showing a configuration example of the recovery container 54. FIG. 4B is a plan view of the recovery container 54 of FIG. 4A. FIG. 4C is a cross-sectional view showing a cross section taken along line B-B of FIG. 4B. FIG. 5 is a cross-sectional view showing the pre-processing kit in a state in which the separation container 50 and the recovery container 54 are placed on top of each other.

The separation container 50 is for separating components of characteristics in a liquid sample by filtering the liquid sample, and is a cylindrical container having internal space 50a for containing a liquid sample and a reagent as shown in FIGS. 3A to 3C. An inner diameter of the internal space 50a is, for example, about 5 to 10 mm, or preferably about 6 to 7 mm. A separation layer 52 is provided at the bottom of the internal space 50a. The separation layer 52 is, for example, a separation agent or a separation film having a function of selectively separating specific components in a sample by physically or chemically reacting with the specific components in the sample passing through the separation layer 52.

As a separation agent which constitutes separation layer 52, for example, ion exchange resin, silica gel, cellulose, activated carbon, and the like can be used. Further, as the separation film, for example, a polytetrafluoroethylene (PTFE) film, a nylon film, a polypropylene film, a polyvinylidene fluoride (PVDF) film, an acrylic copolymer film, a mixed cellulose film, a nitrocellulose film, a polyether sulfone film, an ion exchange film, a glass fiber film, and the like can be used.

As a deproteinization filter (separation film) for removing protein in a sample by filtration, PTFE, an acrylic copolymer film, and the like can be used. In this case, a prefilter (not shown) may be provided on an upper side of the separation layer 52 in order to prevent clogging of the deproteinization filter. As such a prefilter, for example, a nylon film, a polypropylene film, a glass fiber film, and the like can be used. The prefilter is for removing an insoluble matter or a foreign matter having a relatively large particle size from a sample. This prefilter can prevent the deproteinization filter from being clogged by an insoluble matter or a foreign matter having a relatively large particle size.

On an upper surface of the separation container 50, an opening 50b for injecting a liquid sample or a reagent is formed. Further, on a lower surface of the separation container 50, an extraction port 50d for extracting a sample having passed through the separation layer 52 is formed. At an upper portion of an outer peripheral surface of the separation container 50, a collar portion 50c to be engaged with the holding portion 25 of the carrying arm 24 is formed so as to protrude in the circumferential direction.

At the central portion of the outer peripheral surface of the separation container 50, a skirt portion 51 that becomes in contact with an edge of the filtration port 30 when the separation container 50 is accommodated in the filtration port 30 together with the recovery container 54 is provided. The skirt portion 51 protrudes in the circumferential direction from the outer peripheral surface of the separation container 50, and has a cross section formed in an L shape in a manner extending downward from there. In this manner, certain space is formed between the skirt portion 51 and the outer peripheral surface of the separation container 50.

As shown in FIGS. 4A to 4C and FIG. 5, the recovery container 54 is a bottomed cylindrical container that accommodates a lower portion of the separation container 50 and recovers a liquid sample extracted from the extraction port 50d of the separation container 50. On an upper surface of the recovery container 54, an opening 54b into which the lower portion of the separation container 50 is inserted is formed. Inside the recovery container 54, internal space 54a which accommodates a portion of the separation container 50 lower than the skirt portion 51 is formed. Like the separation container 50, at an upper portion of an outer peripheral surface of the recovery container 54, a collar portion 54c to be engaged with the holding portion 25 of the carrying arm 24 is formed so as to protrude in the circumferential direction.

In a state where the separation container 50 and the recovery container 54 are placed on top of each other as shown in FIG. 5, an upper part of the recovery container 54 enters the inside of the skirt portion 51. An outer diameter of the separation container 50 is smaller than an inner diameter of the recovery container 54. In this manner, a slight gap is formed between the outer peripheral surface of the separation container 50 housed in the internal space 54a of the recovery container 54 and the inner peripheral surface of the recovery container 54. The separation container 50 and the recovery container 54 are installed in the container holding unit 12 in a state where the lower portion of the separation container 50 is accommodated in the recovery container 54 (the state of FIG. 5).

Three notches 54d are formed on an edge of the upper surface of the recovery container 54. Therefore, even in a state where the upper surface of the recovery container 54 abuts on the inner surface of the skirt portion 51 as the separation container 50 and the recovery container 54 are placed on top of each other as shown in FIG. 5, the inside and the outside of the recovery container 54 can communicate with each other via the notch 54d. However, the number of the notches 54d is not limited to three, and may be two or less, or four or more. Further, the configuration is not limited to the notch 54d, and may be, for example, a configuration in which a small hole is formed.

Referring again to FIG. 2, the filtration port 30 is provided inside the container holding unit 12. That is, an annular or arc-like holding area is formed by a plurality of the container racks 16 arranged side by side on the outer periphery of the filtration port 30, and a plurality of the separation containers 50 and the recovery containers 54 are held in the holding area. As described above, the holding area of the separation container 50 and the recovery container 54 is formed in an annular shape or an arc shape, and the installation space of the filtration port 30 is secured in the empty space at the central portion of the holding area. In this manner, a more compact configuration can be obtained.

In particular, in the present embodiment, since the separation container 50 and the recovery container 54 placed on top of each other are held in the holding area, it is not necessary to provide the holding areas separately for the separation container 50 and the recovery container 54. Therefore, a larger number of the separation containers 50 and the recovery containers 54 can be held in a small holding area. In this manner, the holding area of the separation container 50 and the recovery container 54 can be reduced, and a more compact configuration can be obtained.

Further, by providing the filtration port 30 at the center of the holding area formed in an annular or arc shape, a distance between a plurality of the separation containers 50 and the recovery containers 54 held in the holding area and the filtration port 30 can be relatively shortened. In this manner, the time for carrying the separation container 50 and the recovery container 54 to the filtration port 30 can be shortened, and the pre-processing efficiency can be improved.

The filtration port 30 constitutes a filtration unit that causes the separation layer 52 to separate a liquid sample by applying pressure to a sample in the separation container 50. In the present embodiment, for example, two of the filtration ports 30 are provided side by side on a path of the holding portion 25 of the carrying arm 24. The separation container 50 and the recovery container 54 placed on top of each other as shown in FIG. 5 are installed in each of the filtration ports 30, and a sample separated by the separation layer 52 in the separation container 50 by negative pressure is recovered in the recovery container 54. However, the configuration is not limited to one in which the separation container 50 and the recovery container 54 placed on top of each other are installed in each of the filtration ports 30, and may be one in which the separation container 50 and the recovery container 54 are installed individually. Further, the number of the filtration ports 30 is not limited to two, and may be one or three or more.

Three of the stirring ports 36a are provided, for example, side by side on a path of the holding portion 25 of the carrying arm 24 in a stirring portion 36 provided in the vicinity of the container holding unit 12. The stirring portion 36 has a mechanism for periodically operating each of the stirring ports 36a individually in a horizontal plane. By such a mechanism, a sample in the separation container 50 disposed in each of the stirring ports 36a can be stirred. However, the number of the stirring ports 36a is not limited to three, and may be two or less, or four or more.

The temperature control ports 38 and 40 are provided, for example, in a thermally conductive block whose temperature is controlled by a heater and a Peltier element, and a temperature of the separation container 50 or the recovery container 54 accommodated in the temperature control ports 38 and 40 is controlled at a certain temperature. The temperature control port 38 is for the separation container 50, and for example, four of the temperature control ports 38 are arranged side by side on the path of the holding portion 25 of the carrying arm 24. The temperature control port 40 is for the recovery container 54, and, as similar to the temperature control port 38 for the separation container 50, for example, four of the temperature control ports 40 are arranged side by side on the path of the holding portion 25 of the carrying arm 24. However, the number of the temperature control ports 38 and 40 is not limited to four, and may be three or less, or five or more.

Figure 6A:
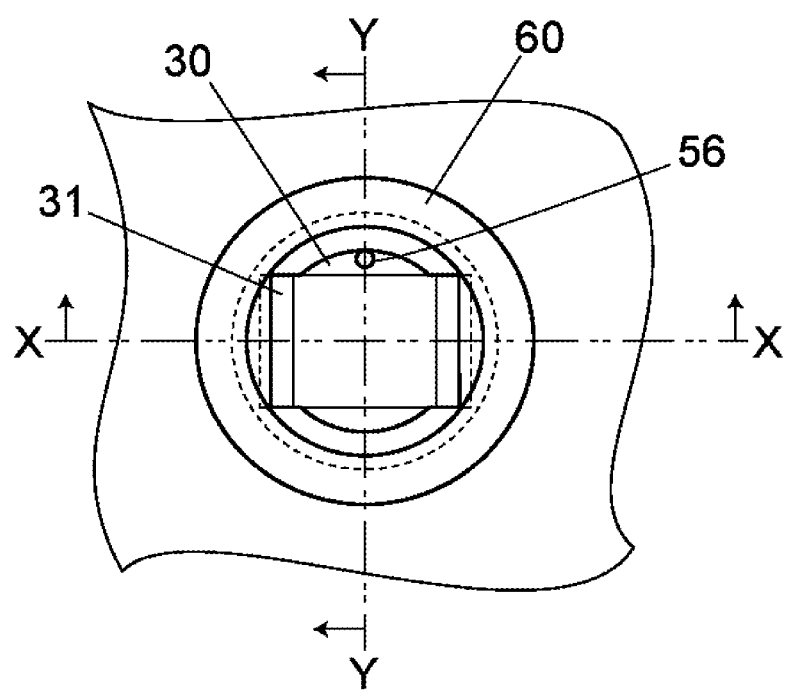
FIG. 6A is a plan view showing a configuration example of a filtration port.
Figure 6B:
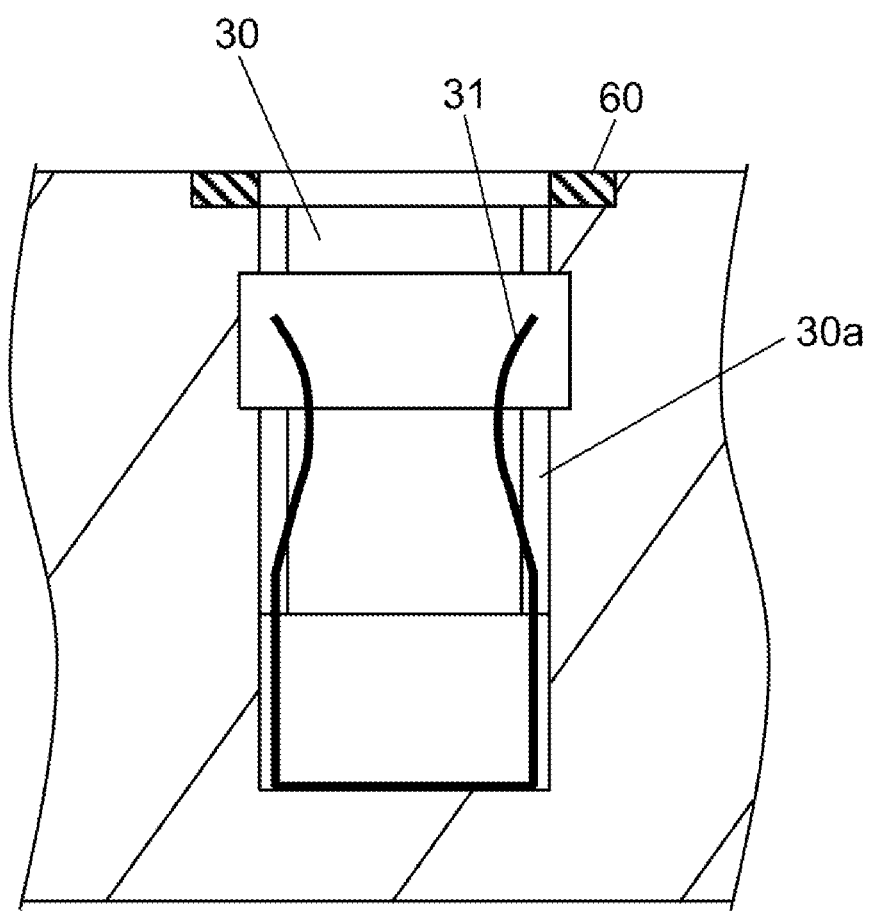
FIG. 6B is a cross-sectional view showing a cross section taken along line X-X in FIG. 6A.
Figure 6C:
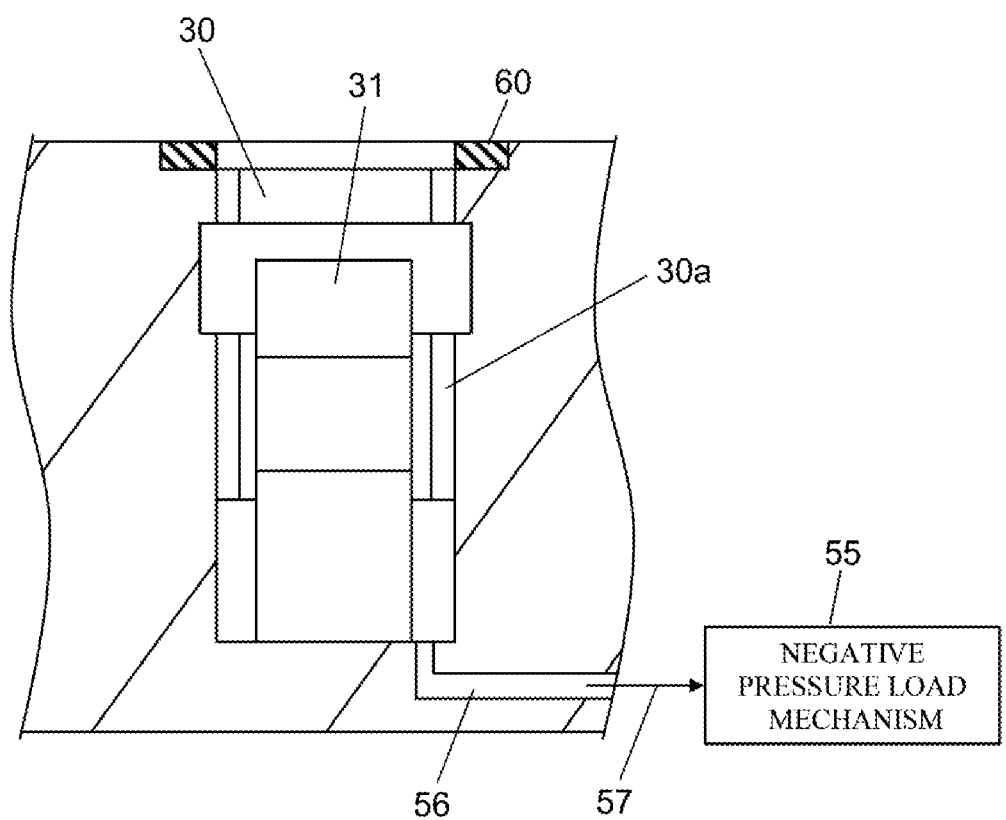
FIG. 6C is a cross-sectional view showing a cross section taken along line Y-Y of FIG. 6A.
Figure 6D:
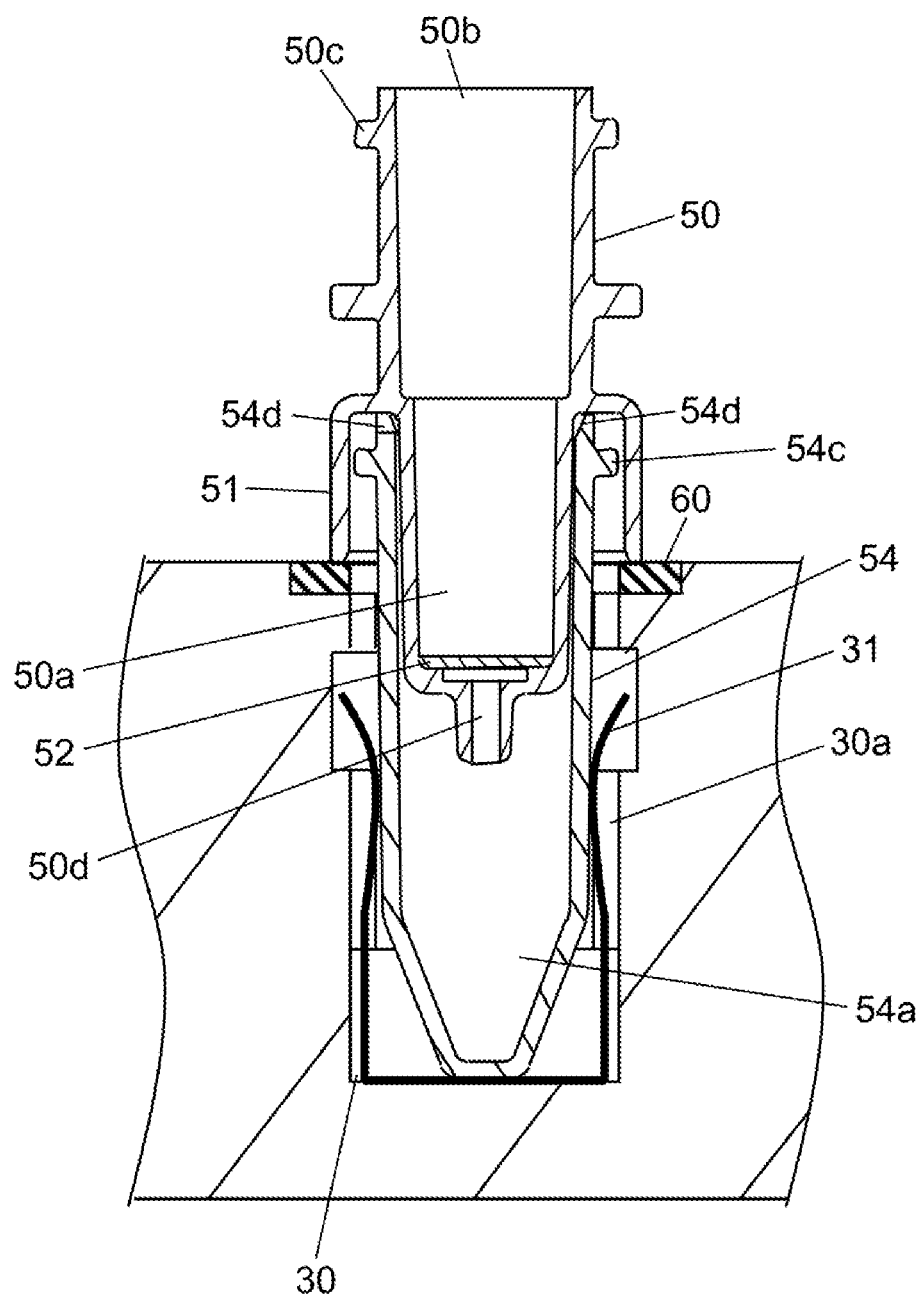
FIG. 6D is a cross-sectional view showing a state where a pre-processing kit is installed in the filtration port.

FIG. 6A is a plan view showing a configuration example of the filtration port 30. FIG. 6B is a cross-sectional view showing a cross section taken along line X-X in FIG. 6A. FIG. 6C is a cross-sectional view showing a cross section taken along line Y-Y of FIG. 6A. FIG. 6D is a cross-sectional view showing a state where a pre-processing kit is installed in the filtration port 30.

The filtration port 30 includes, for example, a recess, and the recess constitutes an installation space 30a for installing the pre-processing kit. That is, as shown in FIG. 6D, the separation container 50 and the recovery container 54 carried from the container holding unit 12 by the carrying arm 24 are installed in the installation space 30a in a state of being placed on top of each other. At this time, the recovery container 54 is accommodated in the installation space 30a first, and then the lower portion of the separation container 50 is accommodated in the internal space 54a of the recovery container 54.

In the filtration port 30, a holding member 31 for holds by sandwiching the recovery container 54. The holding member 31 is, for example, a U-shaped metal member whose upper side is opened, and two arm parts extending upward constitute two leaf springs which can be elastically displaced in an inner diameter direction of the filtration port 30. The two leaf spring portions of the holding member 31 have, for example, a curved or bent shape which is recessed inward so that a distance between an upper end and a lower end is narrowest. A distance between the two leaf spring portions is larger than an outer diameter of the recovery container 54 at the upper end and lower end, and smaller than the outer diameter of the recovery container 54 at a portion at which the distance is narrowest.

When the recovery container 54 is inserted into the installation space 30a of the filtration port 30 due to the shape of the holding member 31 as described above, the two leaf springs of the holding member 31 are opened in accordance with lowering of the recovery container 54, and the recovery container 54 is held in the installation space 30a by its elastic force. The recovery container 54 is uniformly pressed by the two leaf spring portions of the holding member 31 from two directions facing each other, and is held at the central portion of the installation space 30a. The holding member 31 is fixed in the installation space 30a and does not float with the recovery container 54 when the recovery container 54 is taken out.

An elastic ring-shaped sealing member 60 is provided at an edge of a top opening of the filtration port 30. The sealing member 60 is fitted, for example, in a recess provided at the edge of the top opening of the filtration port 30. A material of the sealing member 60 is, for example, an elastic material, such as silicone rubber or ethylene-propylene-diene rubber (EPDM). When the recovery container 54 and the separation container 50 are installed in the installation space 30a of the filtration port 30, a lower end of the skirt portion 51 of the separation container 50 abuts on the sealing member 60, and the installation space 30a becomes in a state of being sealed by the skirt portion 51. However, a contact portion with the sealing member 60 in the separation container 50 is not limited to one configured by a member having a shape, such as that of the skirt portion 51, and may be configured by contact portions having other various shapes, such as that of a flange portion.

A channel 56 for pressure reduction communicates with the installation space 30a from a bottom surface of the filtration port 30. A channel 57 of a negative pressure load mechanism 55 is connected to the channel 56. The negative pressure load mechanism 55 includes, for example, a vacuum pump, and constitutes a negative pressure load unit that applies a negative pressure to the inside of the installation space 30a. When pressure in the installation space 30a is reduced by the negative pressure load mechanism 55 in a state where the separation container 50 and the recovery container 54 are accommodated in the filtration port 30, the inside of the installation space 30a becomes to have negative pressure.

The internal space 54a of the recovery container 54 communicates with the installation space 30a which has negative pressure, via the notch 54d of the recovery container 54 and the gap between the inner peripheral surface of the recovery container 54 and the outer peripheral surface of the separation container 50. Since the upper surface of the separation container 50 is open to the atmosphere, a pressure difference is generated between the internal space 50a of the separation container 50 and the internal space 54a of the recovery container 54 via the separation layer 52. Therefore, in a sample contained in the internal space 50a of the separation container 50, only a component capable of passing through the separation layer 52 is separated by the separation layer 52 due to the pressure difference, and extracted to the internal space 54a side of the recovery container 54.

Figure 7:
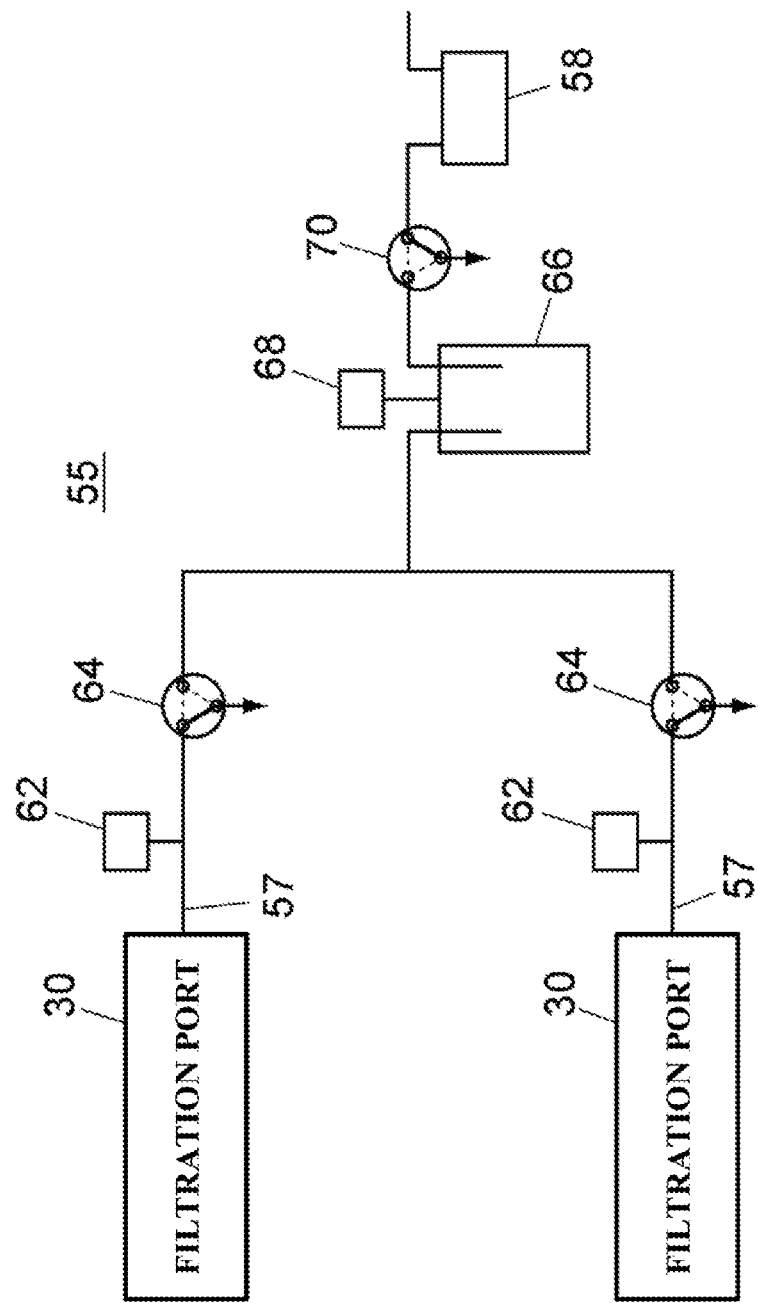
FIG. 7 is a schematic view showing a configuration example of a negative pressure load mechanism.

FIG. 7 is a schematic view showing a configuration example of the negative pressure load mechanism 55. The two filtration ports 30 are connected to a common vacuum tank 66. Each of the filtration ports 30 and the vacuum tank 66 are connected by the channel 57, and each of the channels 57 is provided with a pressure sensor 62 and a three-way valve 64. Pressure in the installation space 30a of each of the filtration ports 30 is detected by each of the pressure sensors 62. Each of the three-way valves 64 can switch to any of a state where the filtration port 30 and the vacuum tank 66 are connected, a state where the filtration port 30 side of the channel 57 is opened to the atmosphere (the state of FIG. 7), and a state where an end on the filtration port 30 side of the channel 57 is sealed.

To the vacuum tank 66, a pressure sensor 68 is connected, and also a vacuum pump 58 is connected via a three-way valve 70. Therefore, by switching the three-way valve 70, the vacuum pump 58 can be connected to the vacuum tank 66 as needed, and pressure in the vacuum tank 66 can be adjusted.

When extraction processing of a liquid sample is executed in any of the filtration ports 30, the filtration port 30 and the vacuum tank 66 are connected, and adjustment is made so that a value of the pressure sensor 62 that detects pressure in the installation space 30a of the filtration port 30 becomes a predetermined value. After the above, an end of the channel 57 on the filtration port 30 side is sealed. In this manner, the installation space 30a of the filtration port 30 becomes a closed system, and the reduced pressure state in the installation space 30a is maintained, so that extraction of a sample is performed.

Referring back to FIG. 2, the pre-processing apparatus 1 is provided with a sample transfer unit 42 for transferring a liquid sample extracted in the recovery container 54 to the autosampler 101 side. The sample transfer unit 42 includes a moving unit 44 that moves in one direction (an arrow direction in FIG. 2) in the horizontal plane, and the transfer port 43 for installing the recovery container 54 is provided on an upper surface of the moving unit 44. The moving unit 44 moves, for example, by operation of a drive mechanism having a rack and pinion mechanism.

When transfer of a liquid sample to the autosampler 101 side is not performed, the transfer port 43 is disposed on the path of the holding portion 25 of the carrying arm 24 (a position shown by the solid line in FIG. 2). In this state, installation of the recovery container 54 in the transfer port 43 by the carrying arm 24 and retrieval of the recovery container 54 from the transfer port 43 are performed.

When transfer of a liquid sample to the autosampler 101 side is performed, the moving unit 44 moves toward the outside of the pre-processing apparatus 1 after the recovery container 54 containing the extracted liquid sample is installed in the transfer port 43, and the transfer port 43 is disposed at a position adjacent to the autosampler 101 (a position shown by a broken line in FIG. 2). In this state, a probe for sampling provided in the autosampler 101 sucks a liquid sample in the recovery container 54.

When the suction of a liquid sample by the autosampler 101 is finished, the moving unit 44 is returned to the original position (the position shown by the solid line in FIG. 2), and the recovery container 54 is retrieved by the carrying arm 24. The used recovery container 54 is carried by the carrying arm 24 to the discard port 34 and discarded. The discard port 34 is disposed in the vicinity of the dispensing port 32 on the path of the holding portion 25 of the carrying arm 24, and the used separation container 50 and recovery container 54 are discarded.

On the path of the sample dispensing probe 20a, the cleaning port 45 for cleaning the sample dispensing probe 20a is provided. Note that, although not shown, a cleaning port for cleaning the reagent dispensing probe 26a is provided on the path of the reagent dispensing probe 26a.

3. Configuration of Pre-Processing System

Figure 8:
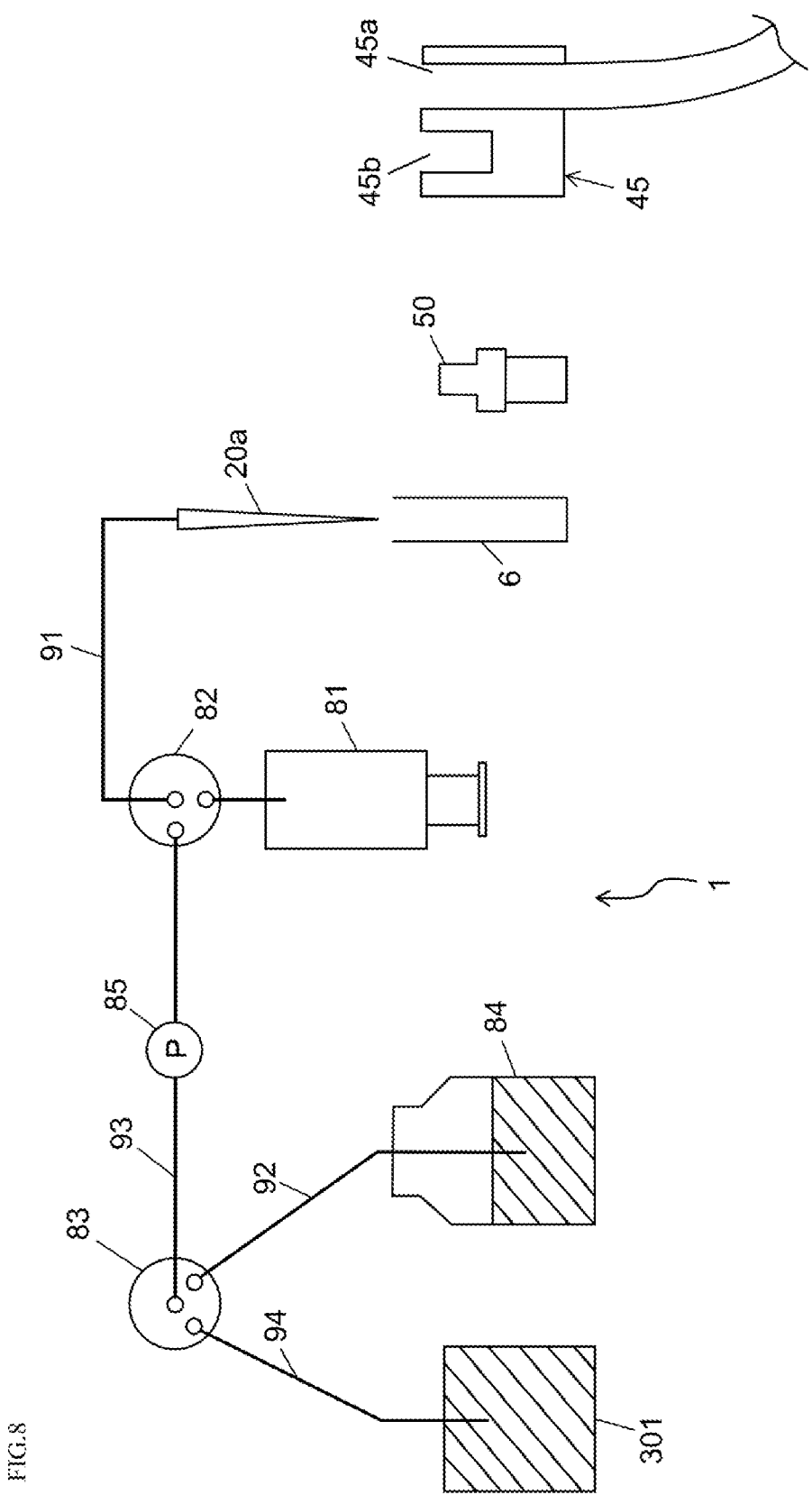
FIG. 8 is a diagram schematically showing a configuration example of a pre-processing system.

FIG. 8 is a diagram schematically showing a configuration example of the pre-processing system.

The pre-processing system includes, as described above, the pre-processing apparatus 1 and the cell culture apparatus 300 (culture tank 301). This pre-processing system is a system for performing the pre-processing of the liquid sample in the cell culture apparatus 300 in an automated manner.

The pre-processing apparatus 1 includes a syringe pump 81 as an example of a pump, three-way valves 82 and 83, a cleaning solution storage unit 84, and a tube pump 85 in addition to the sample dispensing probe 20a and the cleaning port 45 described above.

The sample dispensing probe 20a is movable to a position at which various types of processing are performed in each of the sample container 6, the separation container 50, and the cleaning port 45 by the operation of the sample dispensing arm 20 (see FIG. 2).

In the cleaning port 45, a drain 45a for discarding unnecessary liquid and a recess 45b capable of storing a cleaning solution are formed.

The syringe pump 81 is a pump for causing a liquid sample to be discharged from the sample dispensing probe 20a, or causing a liquid sample to be sucked into the sample dispensing probe 20a. One end of a channel 91 is connected to the syringe pump 81, and the other end of the channel 91 is connected to the sample dispensing probe 20a. The three-way valve 82 is interposed in the middle of the channel 91.

The cleaning solution storage unit 84 contains a cleaning solution in the inside. The cleaning solution is, for example, pure water. One end of a channel 92 is disposed in the cleaning solution storage unit 84. The other end of the channel 92 is connected to the three-way valve 83.

One end of a channel 93 is connected to the three-way valve 83. The other end of the channel 93 is connected to the three-way valve 82.

The tube pump 85 is interposed in the middle of the channel 93. The tube pump 85 is a pump for sending out a cleaning solution in the cleaning solution storage unit 84 or a liquid sample in the culture tank 301 provided in the cell culture apparatus 300. The culture tank 301 is an example of a culture medium storage unit.

The culture tank 301 contains a culture medium as a liquid sample. One end of a channel 94 is connected to the culture tank 301. The other end of the channel 94 is connected to the three-way valve 83.

In the pre-processing system, three-way valves 82 and 83 constitute a switching unit. The three-way valve 82 operates to switch between a state (first state) in which the sample dispensing probe 20a and the syringe pump 81 communicate with each other through the channel 91, and a state (second state) in which the channel 91 and the channel 93 communicate with each other. Further, the three-way valve 83 operates to switch between a state (third state) in which the channel 93 and the channel 92 communicate with each other or a state (fourth state) in which the channel 93 and the channel 94 communicate with each other.

That is, in the pre-processing system, when the three-way valve 82 is in the first state, switching is made to a state where the sample dispensing probe 20a and the syringe pump 81 communicate with each other via the channel 91. Further, when the three-way valve 82 is in the second state, and the three-way valve 83 is in the fourth state, switching is made to a state where the sample dispensing probe 20a and the culture tank 301 communicate with each other via the channels 91, 93, and 94. Further, when the three-way valve 82 is in the second state, and the three-way valve 83 is in the third state, switching is made to a state where the sample dispensing probe 20a and the cleaning solution storage unit 84 communicate with each other via the channels 91, 93, and 92.

4. Electrical Configuration of Analysis System

Figure 9:
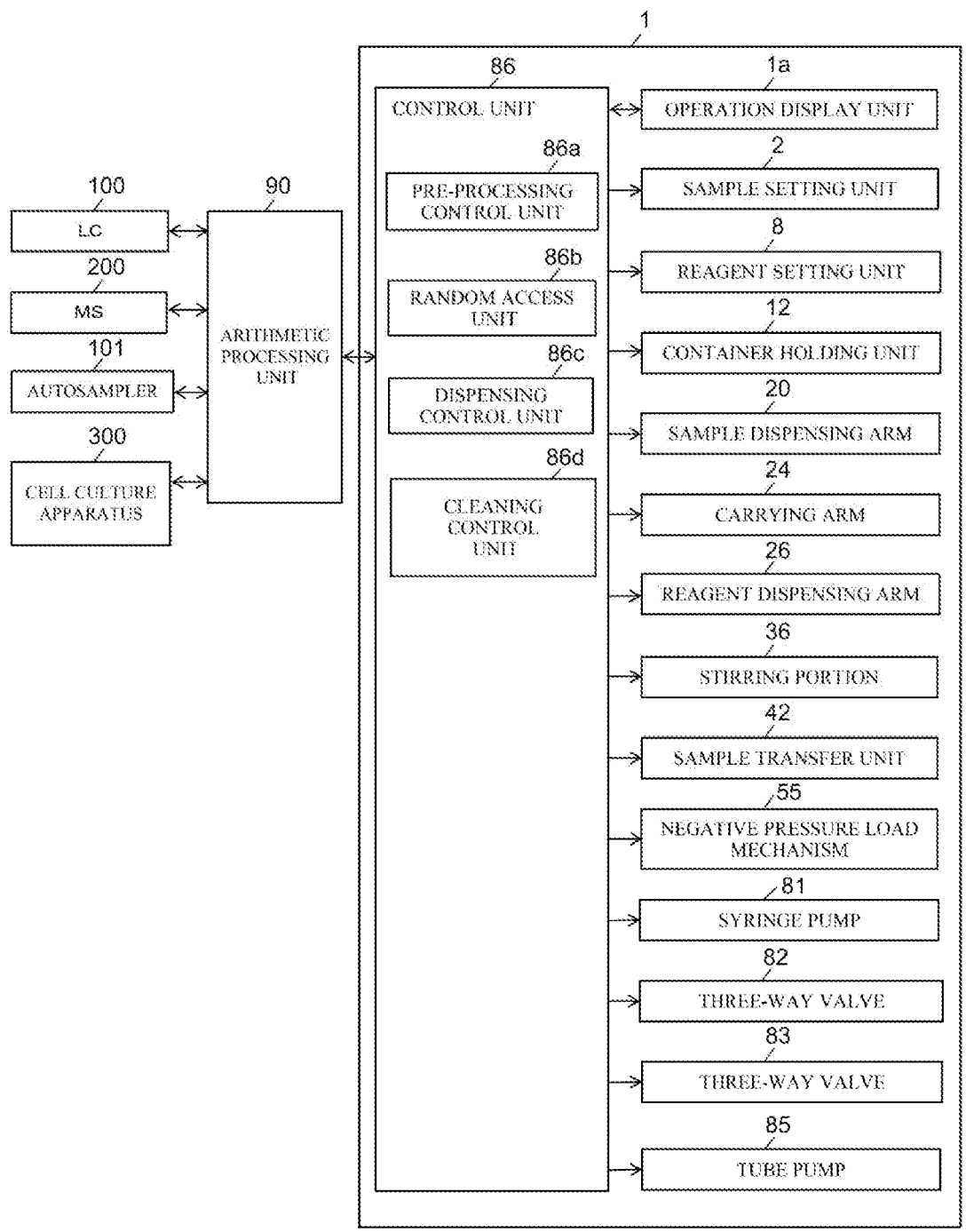
FIG. 9 is a block diagram showing an example of an electrical configuration of an analysis system.

FIG. 9 is a block diagram showing an example of an electrical configuration of the analysis system. The analysis system includes a pre-processing system (the cell culture apparatus 300 and the pre-processing apparatus 1).

In description below, "port" refers to any of a plurality of types of ports, such as the filtration port 30, the dispensing port 32, the stirring port 36a, the temperature control ports 38 and 40, and the transfer port 43 where the separation container 50 or the recovery container 54 is installed.

The pre-processing apparatus 1 includes an operation display unit 1a and a control unit 86 in addition to the above-described configuration. The operation display unit 1a includes, for example, a touch panel.

Operation of the operation display unit 1a, the sample setting unit 2, the reagent setting unit 8, the container holding unit 12, the sample dispensing arm 20, the carrying arm 24, the reagent dispensing arm 26, the stirring portion 36, the sample transfer unit 42, the negative pressure load mechanism 55, the syringe pump 81, the three-way valves 82 and 83, and the tube pump 85 is controlled by the control unit 86.

The control unit 86 includes, for example, a central processing unit (CPU), and the CPU functions as a pre-processing control unit 86a, a random access unit 86b, a dispensing control unit 86c, a cleaning control unit 86d, and the like by executing a program.

The control unit 86 is connected to, for example, an arithmetic processing unit 90 configured with a personal computer (PC) or a dedicated computer, and an analyst can manage the pre-processing apparatus 1 via the arithmetic processing unit 90. The arithmetic processing unit 90 is connected not only to the pre-processing apparatus 1 but also to the LC 100 and MS 200 for analyzing a sample subjected to pre-processing in the pre-processing apparatus 1, the autosampler 101 for injecting a sample to the LC 100, and the like. These apparatuses can be interlocked and automatically controlled by the arithmetic processing unit 90.

As described above, a plurality of the sample containers 6 are installed in the sample setting unit 2, and liquid samples stored in the sample containers 6 are sequentially dispensed into the separation container 50, and the separation container 50 and the recovery container 54 are carried to a port corresponding to the pre-processing to be executed for the liquid samples. When the separation container 50 or the recovery container 54 is installed at each port, the pre-processing control unit 86a executes the pre-processing at the port.

The random access unit 86b checks a situation of the pre-processing in each port, and controls operation of the carrying arm 24 so as to carry the separation container 50 and the recovery container 54, for which the pre-processing in the port is finished, to a port for next pre-processing. That is, the random access unit 86b checks the pre-processing to be performed next on each liquid sample, checks the availability of a port corresponding to the pre-processing, and if there is empty space, the separation container 50 or the recovery container 54 containing the liquid sample is carried to the port. Further, in a case where there is no available port corresponding to pre-processing to be performed next for each liquid sample, the random access unit 86b causes the target separation container 50 or recovery container 54 to be carried to the port as soon as the port becomes available.

The dispensing control unit 86c performs control relating to dispensing operation of a liquid sample and a reagent. The dispensing operation includes operation of causing the sample dispensing probe 20a to suck a liquid sample from the inside of the cell culture apparatus 300 and discharging the liquid sample into the sample container 6, operation of causing the sample dispensing probe 20a to suck a liquid sample from the inside of the sample container 6 and discharging the liquid sample into the separation container 50, and operation of causing the reagent dispensing probe 26a to suck a reagent from the inside of the reagent container 10 and discharging the reagent into the separation container 50.

The cleaning control unit 86d performs control relating to cleaning operation for the sample dispensing probe 20a and a channel communicating with the sample dispensing probe 20a.

When analysis of a sample is performed, an analyst operates the operation display unit 1a to select an analysis item of a sample. The analysis item is selected, for example, by a component name to be analyzed in the LC 100 or the MS 200. Then, by operating the operation display unit 1a, the analyst can set and select the pre-processing necessary to execute the selected analysis item. That is, for the selected analysis item, one or more pieces of optional pre-processing can be selected and set to be executed in the pre-processing apparatus 1.

The pre-processing control unit 86a, the random access unit 86b, and the dispensing control unit 86c control the pre-processing units configured with ports, the sample dispensing arm 20, the carrying arm 24, the reagent dispensing arm 26, the syringe pump 81, the three-way valves 82 and 83, the tube pump 85, and the like based on the setting contents. At this time, control is performed so as to execute a plurality of types of pre-processing set for different samples at the same time and in parallel. Further, the cleaning control unit 86d controls the syringe pump 81, the three-way valves 82 and 83, the tube pump 85, and the like to appropriately clean the sample dispensing arm 20 and the like.

5. Control Operation by Control Unit

Hereinafter, control operation of the control unit 86 and operation of each member in the pre-processing system will be described.

When various settings are performed by an analyst, whether or not the dispensing port 32 is available is first checked by control of the random access unit 86b. If the dispensing port 32 is available, the unused separation container 50 for containing a liquid sample is taken out of the container holding unit 12 by the carrying arm 24 under the control of the random access unit 86b and installed in the dispensing port 32. In this manner, the separation container 50 is disposed at a dispensing position. At this time, the unused sample container 6 is set in the sample setting unit 2.

Note that although the separation container 50 and the recovery container 54 are placed on top of each other in the container holding unit 12 (the state of FIG. 5), the carrying arm 24 holds only the separation container 50 on the upper side with the holding portion 25, and carries the separation container 50 to the dispensing port 32.

Figure 10A:
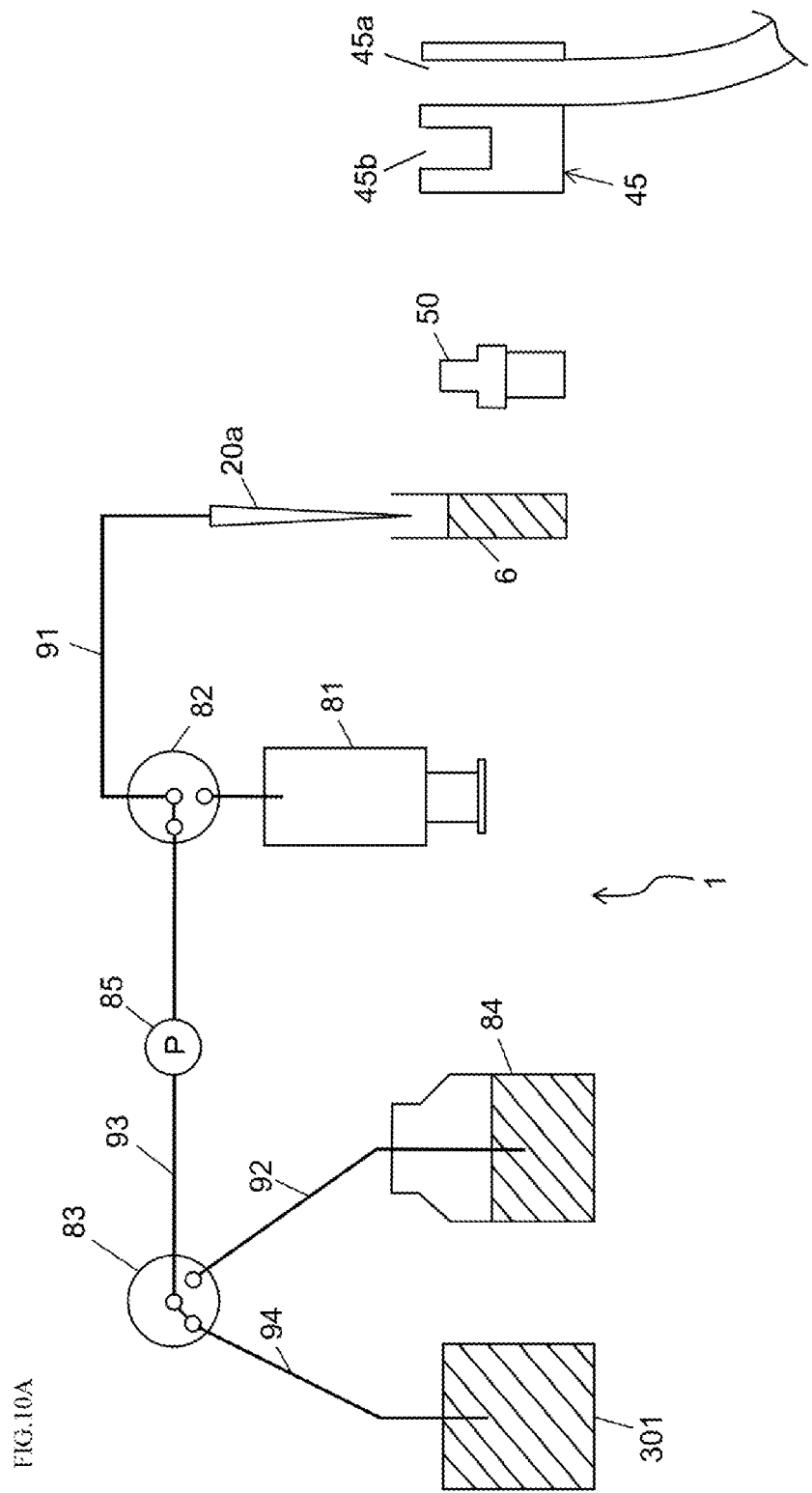
FIG. 10A is a diagram schematically showing a configuration example of the pre-processing system, showing a state in which a liquid sample is introduced from a culture tank into a sample container.

From this state, as shown in FIG. 10A, the dispensing control unit 86c discharges a liquid sample in the culture tank 301 from the sample dispensing probe 20a and introduces it into the sample container 6.

FIG. 10A is a diagram schematically showing a configuration example of the pre-processing system, showing a state in which a liquid sample is introduced from the culture tank 301 into the sample container 6.

Specifically, the three-way valve 82 is operated by the control of the dispensing control unit 86c to switch to the state (second state) in which the channel 91 and the channel 93 communicate with each other, and the three-way valve 83 is also operated to switch to the state (fourth state) in which the channel 93 and the channel 94 communicate with each other. In this manner, the sample dispensing probe 20a and the culture tank 301 communicate with each other through the channels 91, 93, and 94. Further, the sample dispensing probe 20a is moved onto the sample container 6 installed in the sample setting unit 2 by the control of the dispensing control unit 86c.

Then, the tube pump 85 is driven by the control of the dispensing control unit 86c, and a liquid sample in the culture tank 301 is discharged from the sample dispensing probe 20a via the channel 94, the channel 93, and the channel 91, and introduced into the sample container 6.

At this time, a predetermined amount of a liquid sample is introduced into the sample container 6 in a state in which a tip of the sample dispensing probe 20a does not contact a liquid level of the liquid sample stored in the sample container 6. For example, about 500 μL of a liquid sample is introduced into the sample container 6.

Figure 10B:
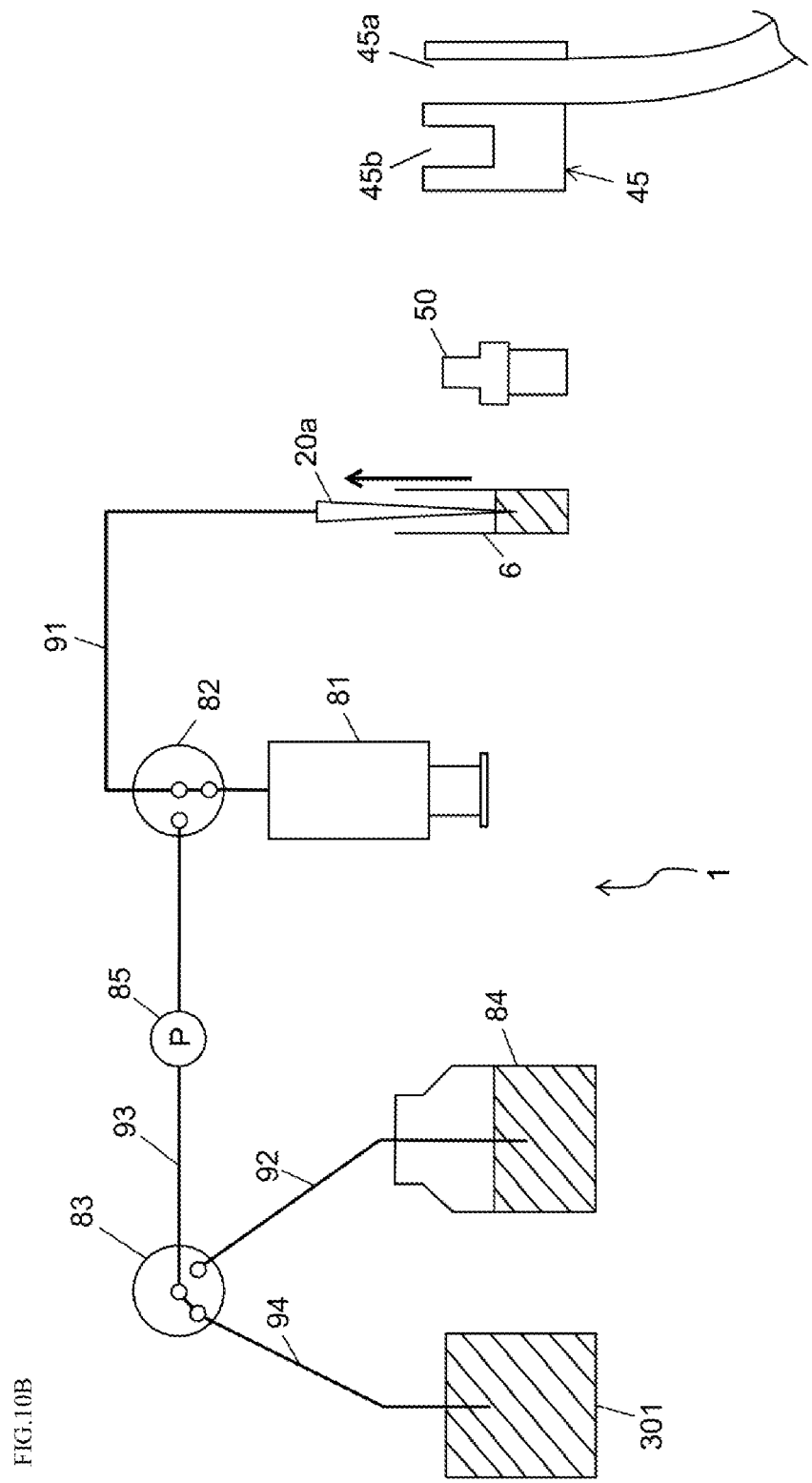
FIG. 10B is a diagram schematically showing a configuration example of the pre-processing system, showing a state in which a liquid sample is sucked into a sample dispensing probe from the inside of the sample container.

Next, as shown in FIG. 10B, a liquid sample is sucked by the sample dispensing probe 20a by the control of the dispensing control unit 86c.

FIG. 10B is a view schematically showing a configuration example of the pre-processing system, showing a state where a liquid sample is sucked from the inside of the sample container 6 to the sample dispensing probe 20a.

Specifically, switching is made to the state (first state) in which the three-way valve 82 is operated by the control of the dispensing control unit 86c and the sample dispensing probe 20a and the syringe pump 81 communicate with each other via the channel 91. In this manner, the sample dispensing probe 20a and the syringe pump 81 communicate with each other through the channel 91. Note that the three-way valve 83 is not operated, and the state (fourth state) in which the channel 93 and the channel 94 communicate with each other is maintained.

Further, the sample dispensing probe 20a is lowered by the control of the dispensing control unit 86c. The sample dispensing probe 20a has a capacitance liquid level detection function. The dispensing control unit 86c moves down the sample dispensing probe 20a until a tip of the sample dispensing probe 20a contacts a liquid surface of a liquid sample in the sample container 6 by a liquid level detection function of the sample dispensing probe 20a.

Then, the syringe pump 81 is driven by the control of the dispensing control unit 86c, and the liquid sample in the sample container 6 is sucked by the sample dispensing probe 20a.

Figure 10C:
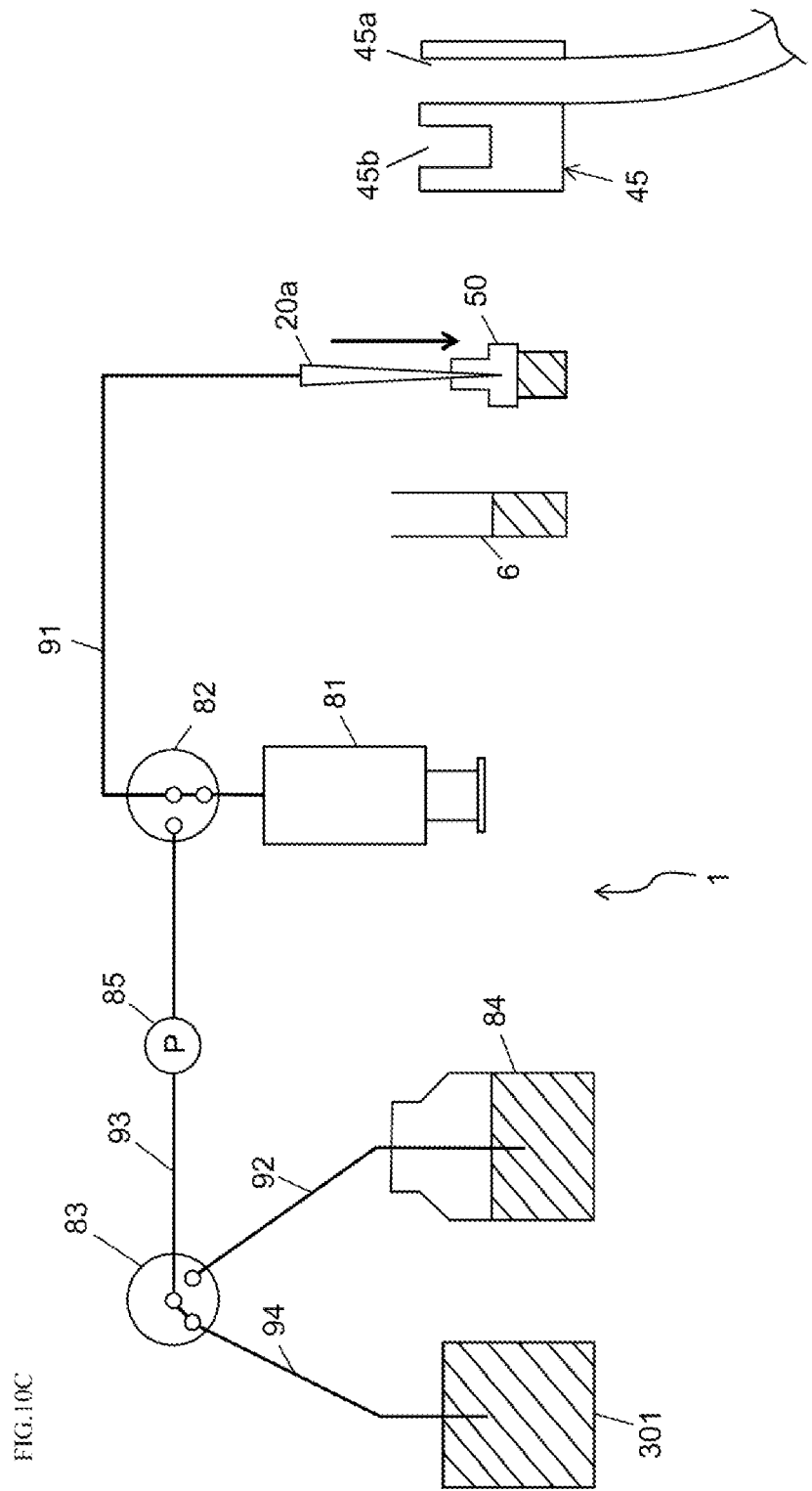
FIG. 10C is a diagram schematically showing a configuration example of the pre-processing system, showing a state in which a liquid sample is discharged from the sample dispensing probe into a separation container.

After the above, as shown in FIG. 10C, the liquid sample is discharged from the sample dispensing probe 20a by the control of the dispensing control unit 86c.

FIG. 10C is a diagram schematically showing a configuration example of the pre-processing system, showing a state in which a liquid sample is discharged from the sample dispensing probe 20a into a separation container 50.

Specifically, the sample dispensing probe 20a is moved onto the separation container 50 disposed at the dispensing position by the control of the dispensing control unit 86c. Then, the syringe pump 81 is driven by the dispensing control unit 86c so that the liquid sample is discharged from the sample dispensing probe 20a, and the liquid sample is introduced into the separation container 50.

At this time, a predetermined amount of the liquid sample is introduced into the separation container 50. For example, about 50 μL of the liquid sample is introduced into the separation container 50.

Figure 10D:
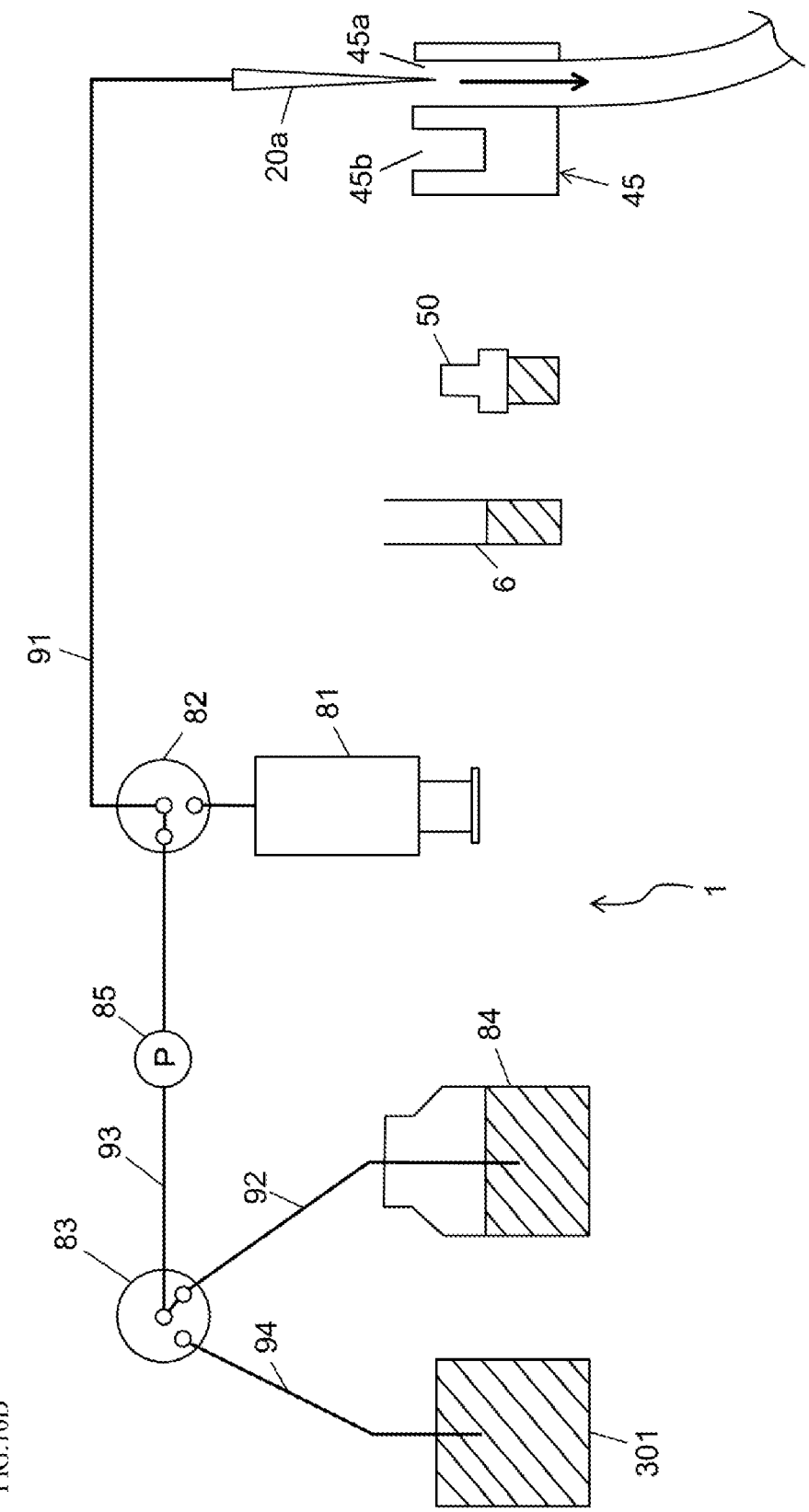
FIG. 10D is a diagram schematically showing a configuration example of the pre-processing system, showing a state in which a channel from a cleaning solution storage unit to the sample dispensing probe is cleaned.

Next, as shown in FIG. 10D, a channel communicating with the sample dispensing probe 20a is cleaned by the control of the cleaning control unit 86d.

FIG. 10D is a diagram schematically showing a configuration example of the pre-processing system, showing a state in which a channel from the cleaning solution storage unit to the sample dispensing probe is cleaned.

Specifically, the three-way valve 82 is operated by the control of the cleaning control unit 86d to switch to the state (second state) in which the channel 91 and the channel 93 communicate with each other, and the three-way valve 83 is also operated to switch to the state (third state) in which the channel 93 and the channel 92 communicate with each other. In this manner, the sample dispensing probe 20a and the cleaning solution storage unit 84 communicate with each other through the channels 91, 93, and 92. Further, the sample dispensing probe 20a is moved onto the drain 45a of the cleaning port 45 by the control of the cleaning control unit 86d.

Then, the tube pump 85 is driven by the control of the cleaning control unit 86d, and a cleaning solution in the cleaning solution storage unit 84 is introduced to the sample dispensing probe 20a via the channel 92, the channel 93, and the channel 91. In this manner, the liquid sample with which the channel 92, the channel 93, and the channel 91 are filled is discharged to the drain 45a of the cleaning port 45 together with the cleaning solution. Then, the inside of the channel 92, the channel 93, the channel 91, and the sample dispensing probe 20a is cleaned by the cleaning solution.

After the above, as shown in FIG. 10E, the sample dispensing probe 20a (the outer surface of the sample dispensing probe 20a) is cleaned.

FIG. 10E is a diagram schematically showing a configuration example of the pre-processing system, showing a state in which the outer surface of the sample dispensing probe 20a is cleaned.

Specifically, the sample dispensing probe 20a is moved onto the recess 45b of the cleaning port 45 by the control of the cleaning control unit 86d. At this time, the tip of the sample dispensing probe 20a is disposed in internal space of the recess 45b of the cleaning port 45.

Then, the tube pump 85 is driven by the control of the cleaning control unit 86d, and a cleaning solution in the cleaning solution storage unit 84 is discharged from the sample dispensing probe 20a via the channel 92, the channel 93, and the channel 91. In this manner, a cleaning solution is stored in the recess 45b of the cleaning port 45. Then, the sample dispensing probe 20a is immersed in the stored cleaning solution. In this manner, the outer surface of the sample dispensing probe 20a is cleaned.

Note that the configuration may be such that a separate cleaning solution storage unit is connected to the syringe pump 81, and, after the sample dispensing probe 20a is cleaned, an operation of cleaning the syringe pump 81 is performed by the cleaning solution storage unit.

Next, as shown in FIG. 10F, the sample dispensing probe 20a is filled with a liquid sample.

FIG. 10F is a diagram schematically showing a configuration example of the pre-processing system, showing a state in which sections from the culture tank 301 to the sample dispensing probe 20a are filled with a liquid sample.

Specifically, the three-way valve 82 is operated by the control of the dispensing control unit 86c to switch to the state (second state) in which the channel 91 and the channel 93 communicate with each other, and the three-way valve 83 is also operated to switch to the state (fourth state) in which the channel 93 and the channel 94 communicate with each other. In this manner, the sample dispensing probe 20a and the culture tank 301 communicate with each other through the channels 91, 93, and 94. Further, the sample dispensing probe 20a is moved onto the drain 45a of the cleaning port 45 by the dispensing control unit 86c.

Then, the tube pump 85 is driven by the control of the dispensing control unit 86c, and a liquid sample in the culture tank 301 is discharged from the sample dispensing probe 20a via the channel 94, the channel 93, and the channel 91. In this manner, the cleaning solution with which the channel 92, the channel 93, and the channel 91 are filled is discharged to the drain 45a of the cleaning port 45. Then, the channel 92, the channel 93, the channel 91, and the sample dispensing probe 20a are filled with the liquid sample.

After the above, the above-described operation is performed on another unused one of the sample containers 6.

Note that the reagent dispensing probe 26a is moved by the control of the dispensing control unit 86c into the separation container 50 into which the liquid sample is introduced, and then a predetermined amount of a reagent is discharged. Then, the separation container 50 in the dispensing port 32 is carried by the carrying arm 24 to the stirring port 36a by the control of the random access unit 86b. Further, stirring processing is performed in the stirring port 36a by the control of the pre-processing control unit 86a. The stirring processing is performed for a predetermined time which is set in advance. In this manner, a sample and a reagent in the separation container 50 and are mixed.

Furthermore, the recovery container 54 is carried to the filtration port 30 by the carrying arm 24 under the control of the random access unit 86b. At this time, the recovery container 54 installed in the filtration port 30 is the recovery container 54 paired with the separation container 50 which is provided in the stirring port 36a and in which stirring processing is being performed, and the recovery container 54 installed in a state in which the separation container 50 in the container holding unit 12 is placed on the recovery container 54.

When the stirring processing in the stirring portion 36 (stirring port 36a) is finished, the separation container 50 is carried from the stirring port 36a to the filtration port 30 by the carrying arm 24 by the control of the random access unit 86b, and the separation container 50 is placed on the recovery container 54 in the filtration port 30 as shown in FIG. 6D. At this time, since the sealing member 60 is crushed by the lower end of the skirt portion 51, airtightness between the lower end of the skirt portion 51 and the sealing member 60 is improved.

Then, the negative pressure load mechanism 55 is operated to apply a load of predetermined negative pressure to the installation space 30a of the filtration port 30 in which the separation container 50 and the recovery container 54 are installed. As a state in which the negative pressure is applied to the installation space 30a of the filtration port 30 is maintained for a certain period of time, a liquid sample in the separation container 50 is filtered, and the liquid sample is extracted to the recovery container 54.

After filtration processing of a sample is finished, the three-way valve 64 (see FIG. 9) is switched so that the inside of the installation space 30a of the filtration port 30 is set at atmospheric pressure. Then, the used separation container 50 is taken out of the filtration port 30 by the holding portion 25 of the carrying arm 24 and discarded to the discard port 34.

After the above, the recovery container 54 in the filtration port 30 is carried by the carrying arm 24 to the sample transfer unit 42 and installed on the transfer port 43. Then, the recovery container 54 is transferred to the autosampler 101 side as the moving unit 44 moves to a position on the adjacent autosampler 101 side (the position shown by the broken line in FIG. 2). On the autosampler 101 side, suction of a liquid sample by a probe for sampling into the recovery container 54 transferred from the sample transfer unit 42 is performed.

The moving unit 44 stops at a position on the autosampler 101 side until sample suction in the autosampler 101 ends, and, when receiving a signal from the autosampler 101 showing that the sample suction has ended, returns to the original position (the position shown by the solid line in FIG. 2). After transfer of a liquid sample is finished, the used recovery container 54 is retrieved from the transfer port 43 by the carrying arm 24 and discarded to the discard port 34.

6. Action and Effect (1) In the present embodiment, a switch can be made between a state in which the sample dispensing probe 20a and the syringe pump 81 communicate with each other through the channel 91 (see FIG. 10B) and a state in which the sample dispensing probe 20a and the culture tank 301 communicate with each other through the channels 91, 93, and 94 (see FIG. 10A) by the operation of the three-way valves 82 and 83. That is, by the operation of the three-way valves 82 and 83, a switch can be made to a state where a liquid sample is introduced from the culture tank 301 to the sample dispensing probe 20a.

For this reason, the liquid sample in the culture tank 301 can be automatically discharged from the sample dispensing probe 20a without requiring the user to directly sample the liquid sample.

As a result, in the pre-processing system, the user's manual sampling work can be omitted, and the user's work can be simplified.

(2) Further, in the present embodiment, as shown in FIG. 10A, the dispensing control unit 86c operates the three-way valves 82 and 83 to set the sample dispensing probe 20a and the culture tank 301 to be in a state of being communicating with each other via the channels 91, 93 and 94, and drives the tube pump 85 to introduce a liquid sample in the culture tank 301 from the sample dispensing probe 20a into the sample container 6. Then, as shown in FIG. 10B, the dispensing control unit 86c operates the three-way valves 82 and 83 to set the sample dispensing probe 20a and the syringe pump 81 to be in a state of being communicating with each other via the channel 91, and drives the syringe pump 81 in this state to cause the liquid sample in the sample container 6 to be sucked into the sample dispensing probe 20a.

For this reason, operation of introducing a liquid sample from the culture tank 301 to the sample container 6 via the sample dispensing probe 20a, and operation of causing the liquid sample to be sucked from the inside of the sample container 6 to the sample dispensing probe 20a can be switched automatically and implemented under the control of the dispensing control unit 86c.

As a result, a series of operations in the pre-processing system can be automated, and the work of the user can be further simplified.

(3) Further, in the present embodiment, after moving the sample dispensing probe 20a onto the separation container 50 disposed at the dispensing position, the dispensing control unit 86c drives the syringe pump 81 to discharge a liquid sample from the sample dispensing probe 20a into the separation container 50.

That is, by discharging a liquid sample from the sample dispensing probe 20a to the separation container 50 by the control of the dispensing control unit 86c, a specific component in the liquid sample can be separated in the separation container 50.

Therefore, in the pre-processing system, the operations from introducing a liquid sample into the sample dispensing probe 20a to separating a specific component in the liquid sample can be automated.

(4) Further, in the present embodiment, a switch can be made to a state in which the sample dispensing probe 20a and the cleaning solution storage unit 84 communicate with each other through the channels 91, 93, and 92 by the operation of the three-way valves 82 and 83 (see FIGS. 10D and 10E).

Therefore, by driving the tube pump 85 in a state where the sample dispensing probe 20a and the cleaning solution storage unit 84 communicate with each other, a cleaning solution in the cleaning solution storage unit 84 can be automatically introduced into the sample dispensing probe 20a.

(5) Further, in the present embodiment, as shown in FIGS. 10D and 10E, the cleaning control unit 86d operates the three-way valves 82 and 83 to set a state in which the sample dispensing probe 20a and the cleaning solution storage unit 84 communicate with each other via the channels 91, 93, and 92, and drives the tube pump 85 to introduce a cleaning solution in the cleaning solution storage unit 84 into the sample dispensing probe 20a, so that the inside of the channel 92, the channel 93, the channel 91, and the sample dispensing probe 20a is cleaned.

For this reason, in the pre-processing system, the operation of cleaning the inside of the channel 92, the channel 93, the channel 91, and the sample dispensing probe 20a can be automated.

(6) Further, in the present embodiment, pre-processing is performed for a culture medium of the culture tank 301 of the cell culture apparatus 300.

Therefore, in the pre-processing for a culture medium of the culture tank 301 of the cell culture apparatus 300, the user's manual sampling work can be omitted, and the user's work can be simplified.

7. Variation

In the above embodiment, description is made on the configuration in which a liquid sample in the culture tank 301 and a cleaning solution in the cleaning solution storage unit 84 are sent out as the tube pump 85 is driven, and a liquid sample in the sample container 6 is sucked to the sample dispensing probe 20a and discharged as the syringe pump 81 is driven. However, the configuration may be such that the tube pump 85 and the syringe pump 81 are configured as one pump, so that the above operations are performed as this one pump is driven.

Further, in the above embodiment, description is made on the configuration in which a sample in the separation container 50 is separated by setting the inside of the installation space 30a of the filtration port 30 to a negative pressure. However, the configuration is not limited to such a configuration, and may be such that a sample in the separation container 50 is separated by pressurizing the inside of the separation container 50.

Further, the configuration is not limited to one in which the control unit 86 of the pre-processing apparatus 1 and the arithmetic processing unit 90 are provided separately, and may be one in which operation of the whole analysis system is controlled by one control unit. Further, the configuration is not limited to one in which a sample subjected to the pre-processing by the pre-processing apparatus 1 is introduced to the LC 100 or the MS 200, and may be one in which the sample is introduced to other apparatuses.

Further, each of the sample containers 6 installed in the sample setting unit 2 may be discarded after use. Then, every time each of the sample containers 6 is discarded, new one of the sample container 6 may be installed in the sample setting unit 2.

Further, the above embodiment states that the operations of introducing a liquid sample into one of a plurality of the sample containers 6 installed in the sample setting unit 2 and sucking the liquid sample from the sample container 6 are repeated. However, the configuration may be such that a liquid sample is introduced into each of a plurality of the sample containers 6 and then the liquid samples in the sample containers 6 are sequentially sucked.

Further, in the above embodiment, the switching unit is described as being configured with the three-way valves 82 and 83. However, the configuration of the switching unit only needs to be one in which communication states of channels can be switched, and is not limited to one in which the switching unit consists of two three-way valves.

Further, the above embodiment states that the separation container 50 is installed at the dispensing position. However, the configuration may be such that, at the dispensing position, a pre-processing kit in which the separation container 50 is placed on the recovery container 54 is installed, and a liquid sample is introduced to the separation container 50 in that state. In this case, the pre-processing kit itself (the separation container 50 and the recovery container 54) is desirably carried every time each processing is performed.

Further, the above embodiment states that the culture tank 301 of the cell culture apparatus 300 is the liquid sample storage unit. However, the liquid sample storage unit is not limited to the culture tank 301 of the cell culture apparatus 300, and may be, for example, a liquid sample storage unit provided in other apparatuses that handle a sample to be measured.

DESCRIPTION OF REFERENCE SIGNS

2 sample setting unit
6 sample container
20*a* sample dispensing probe
50 separation container
81 syringe pump
82, 83 three-way valve
84 cleaning solution storage unit
86 control unit
86*c* dispensing control unit
86*d* cleaning control unit
91, 92, 93 channel
300 cell culture apparatus
301 culture tank 301

The invention claimed is:

1. A pre-processing system for performing pre-processing for a liquid sample from a liquid sample storage unit, the pre-processing system comprising:
   a sample setting unit in which a sample container is installed;
   a probe configured to suck the liquid sample from an inside of the sample container installed in the sample setting unit and discharge the liquid sample to a dispensing position;
   a first pump driven when the probe sucks and discharges the liquid sample;
   the liquid sample storage unit comprising a culture medium storage unit provided in a cell culture apparatus;
   a cleaning solution storage unit configured to store a cleaning solution;
   a first valve configured to switch between a state in which the probe communicates with the first pump and a state in which the probe communicates with the liquid sample storage unit or the cleaning solution storage unit;
   a second valve configured to switch between the state in which the probe communicates with the liquid sample storage unit, and the state in which the probe communicates with the cleaning solution storage unit;
   a second tube pump provided in a channel between the first valve and the second valve, and is configured to be driven when the liquid sample in the culture medium storage unit is sent out to the probe; and
   a dispensing control unit configured to cause the probe to communicate with the first pump by switching the first valve after the liquid sample is introduced to the sample container installed in the sample setting unit via the probe in the state where the probe communicates with the liquid sample storage unit, and, in the state in which the probe communicates with the first pump, drive the first pump so that the liquid sample is sucked from the inside of the sample container to the probe.

2. The pre-processing system according to claim 1, further comprising
   a separation container, the separation container configured to separate a specific component in the liquid sample by filtering the liquid sample is installed at the dispensing position, and
   the dispensing control unit moves the probe, which has sucked the liquid sample, to the dispensing position and drives the first pump to discharge the liquid sample from the probe to the separation container.

3. The pre-processing system according to claim 1, further comprising a cleaning control unit configured to clean the channel from the cleaning solution storage unit to the probe by introducing the cleaning solution into the probe in the state where the probe communicates with the cleaning solution storage unit.

* * * * *